(12) United States Patent
Kheradvar et al.

(10) Patent No.: US 8,133,270 B2
(45) Date of Patent: Mar. 13, 2012

(54) IN-SITU FORMATION OF A VALVE

(75) Inventors: Arash Kheradvar, Blythewood, SC (US); Morteza Gharib, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 874 days.

(21) Appl. No.: 12/008,109

(22) Filed: Jan. 8, 2008

(65) Prior Publication Data
US 2008/0195199 A1  Aug. 14, 2008

Related U.S. Application Data

(60) Provisional application No. 60/879,288, filed on Jan. 8, 2007, provisional application No. 60/930,458, filed on May 16, 2007.

(51) Int. Cl.
*A61F 2/24* (2006.01)
*A61F 2/06* (2006.01)

(52) U.S. Cl. ........................ 623/2.11; 623/1.26

(58) Field of Classification Search ............ 623/2.11, 623/2.12, 2.13, 2.14, 2.15, 2.16, 2.17, 2.18, 623/1.19, 1.26, 23.68, 1.24; 606/191, 192, 606/194

See application file for complete search history.

(56) References Cited

U.S. PATENT DOCUMENTS

| | | |
|---|---|---|
| 3,671,979 A | 6/1972 | Moulopoulos |
| 4,291,420 A | 9/1981 | Reul |
| 4,451,936 A | 6/1984 | Carpentier |
| 4,692,164 A | 9/1987 | Dzemeshkevich |
| 4,759,758 A | 7/1988 | Gabbay |
| 4,787,901 A | 11/1988 | Baykut |
| 4,790,843 A | 12/1988 | Carpentier |
| 4,851,001 A | 7/1989 | Taheri |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona et al. |
| 5,032,128 A | 7/1991 | Alonso |
| 5,037,434 A | 8/1991 | Lane |
| 5,080,668 A | 1/1992 | Bolz |

(Continued)

FOREIGN PATENT DOCUMENTS
EP  0 380 666  8/1990
(Continued)

OTHER PUBLICATIONS
PCT International Search Report and the Written Opinion of The International Searching Authority.
(Continued)

*Primary Examiner* — Corrine M McDermott
*Assistant Examiner* — Christina Lauer
(74) *Attorney, Agent, or Firm* — Tope-McKay & Associates; Marcus Risso

(57) ABSTRACT

The present invention satisfies the long felt need for a more compact and durable valve which may be formed in situ. The present invention provides a self-deployable valve system, a method of delivery, and a method of manufacturing for the self-deployable valve system. The present invention delivers the necessary components for forming a complete valve system in situ. The collapsed subcomponents of the system lack any functional characteristics commonly associated with a valve before being expanded. However, once expanded, the system is transformed into a competent valve for use in a wide variety of applications.

15 Claims, 10 Drawing Sheets

U.S. PATENT DOCUMENTS

| | | | |
|---|---|---|---|
| 5,141,491 A | 8/1992 | Bowald |
| 5,163,953 A | 11/1992 | Vince |
| 5,219,355 A | 6/1993 | Parodi et al. |
| 5,254,127 A | 10/1993 | Wholey et al. |
| 5,282,847 A | 2/1994 | Trescony |
| 5,327,774 A | 7/1994 | Nguyen et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik |
| 5,411,552 A | 5/1995 | Andersen |
| 5,445,626 A | 8/1995 | Gigante |
| 5,469,868 A | 11/1995 | Reger |
| 5,480,423 A | 1/1996 | Ravenscroft et al. |
| 5,500,014 A | 3/1996 | Quijano |
| 5,545,214 A | 8/1996 | Stevens |
| 5,554,185 A | 9/1996 | Block et al. |
| 5,571,175 A | 11/1996 | Vanney |
| 5,591,195 A | 1/1997 | Taheri |
| 5,607,464 A | 3/1997 | Trescony |
| 5,609,626 A | 3/1997 | Quijano |
| 5,643,208 A | 7/1997 | Parodi |
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,749,890 A | 5/1998 | Shaknovich |
| 5,800,506 A | 9/1998 | Perouse |
| 5,824,061 A | 10/1998 | Quijano et al. |
| 5,824,064 A | 10/1998 | Taheri |
| 5,840,081 A | 11/1998 | Andersen |
| 5,855,597 A | 1/1999 | Jayaraman |
| 5,855,601 A | 1/1999 | Bessler |
| 5,855,602 A | 1/1999 | Angell |
| 5,879,320 A | 3/1999 | Cazenave |
| 5,895,419 A | 4/1999 | Tweden et al. |
| 5,910,170 A | 6/1999 | Reimink et al. |
| 5,925,063 A | 7/1999 | Khosravi |
| 5,954,766 A * | 9/1999 | Zadno-Azizi |
| 5,957,949 A * | 9/1999 | Leonhardt |
| 6,010,531 A | 1/2000 | Donlon et al. |
| 6,042,607 A | 3/2000 | Williamson, IV et al. |
| 6,077,298 A | 6/2000 | Tu et al. |
| 6,106,550 A * | 8/2000 | Magovern |
| 6,106,551 A | 8/2000 | Crossett et al. |
| 6,132,473 A | 10/2000 | Williams |
| 6,139,575 A | 10/2000 | Shu et al. |
| 6,168,614 B1 * | 1/2001 | Andersen |
| 6,206,911 B1 * | 3/2001 | Milo |
| 6,283,127 B1 * | 9/2001 | Sterman |
| 6,287,334 B1 | 9/2001 | Moll et al. |
| 6,299,637 B1 | 10/2001 | Shaolian et al. |
| 6,312,447 B1 | 11/2001 | Grimes |
| 6,355,030 B1 | 3/2002 | Aldrich et al. |
| 6,402,780 B2 | 6/2002 | Williamson, IV et al. |
| 6,419,696 B1 | 7/2002 | Ortiz et al. |
| 6,425,916 B1 * | 7/2002 | Garrison et al. ............. 623/2.11 |
| 6,440,164 B1 | 8/2002 | DiMatteo et al. |
| 6,451,054 B1 | 9/2002 | Stevens |
| 6,454,799 B1 | 9/2002 | Schreck |
| 6,458,153 B1 | 10/2002 | Bailey |
| 6,461,366 B1 | 10/2002 | Seguin |
| 6,482,228 B1 | 11/2002 | Norred |
| 6,503,272 B2 | 1/2003 | Duerig et al. |
| 6,508,833 B2 | 1/2003 | Pavcnik et al. |
| 6,530,952 B2 * | 3/2003 | Vesely |
| 6,564,805 B2 | 5/2003 | Garrison et al. |
| 6,569,196 B1 * | 5/2003 | Vesely |
| 6,582,462 B1 * | 6/2003 | Andersen |
| 6,602,286 B1 | 8/2003 | Strecker |
| 6,629,534 B1 | 10/2003 | St. Goar et al. |
| 6,635,085 B1 | 10/2003 | Caffey et al. |
| 6,638,239 B1 | 10/2003 | Bergheim et al. |
| 6,652,578 B2 * | 11/2003 | Baily |
| 6,666,841 B2 | 12/2003 | Gharib et al. |
| 6,666,885 B2 | 12/2003 | Moe |
| 6,666,886 B1 | 12/2003 | Tranquillo et al. |
| 6,669,725 B2 | 12/2003 | Scott |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser |
| 6,730,121 B2 | 5/2004 | Ortiz et al. |
| 6,730,122 B1 | 5/2004 | Pan et al. |
| 6,736,791 B1 | 5/2004 | Tu et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,770,083 B2 | 8/2004 | Sequin |
| 6,780,164 B2 | 8/2004 | Bergheim et al. |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 * | 12/2004 | Seguin |
| 6,830,585 B1 * | 12/2004 | Artof |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,869,444 B2 | 3/2005 | Gabbay |
| 6,872,226 B2 | 3/2005 | Cali et al. |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |

| Patent No. | Date | Inventor |
|---|---|---|
| 6,883,522 B2 | 4/2005 | Spence et al. |
| 6,890,350 B1 | 5/2005 | Walak |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spence et al. |
| 6,896,690 B1 * | 5/2005 | Lambrecht |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 * | 6/2005 | Cribier |
| 6,911,043 B2 | 6/2005 | Myers et al. |
| 6,913,608 B2 | 7/2005 | Liddicoat et al. |
| 6,916,338 B2 | 7/2005 | Speziah |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 * | 10/2005 | Srivastava |
| 6,951,573 B1 | 10/2005 | Dilling |
| 6,955,656 B2 | 10/2005 | Bergheim et al. |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |
| 6,974,474 B2 | 12/2005 | Pavcnik et al. |
| 6,974,476 B2 * | 12/2005 | McGuckin |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,004,176 B2 | 2/2006 | Lau |
| 7,007,396 B2 | 3/2006 | Rudko et al. |
| 7,007,698 B2 | 3/2006 | Thornton |
| 7,011,669 B2 | 3/2006 | Kimblad |
| 7,011,681 B2 | 3/2006 | Vesely |
| 7,011,682 B2 | 3/2006 | Lahsinski et al. |
| 7,018,406 B2 | 3/2006 | Saguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan et al. |
| 7,070,616 B2 | 7/2006 | Majercak et al. |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 7,101,396 B2 | 9/2006 | Artof |
| 7,331,991 B2 | 2/2008 | Kheradvar et al. |
| 7,967,853 B2 | 6/2011 | Eidenschink et al. |
| 2002/0013571 A1 | 1/2002 | Goldfarb et al. |
| 2002/0026216 A1 | 2/2002 | Grimes |
| 2002/0082630 A1 | 6/2002 | Menz et al. |
| 2002/0123802 A1 | 9/2002 | Snyders |
| 2002/0151970 A1 | 10/2002 | Garrison et al. |
| 2002/0183835 A1 | 12/2002 | Taylor et al. |
| 2002/0183838 A1 | 12/2002 | Liddicoat et al. |
| 2002/0198594 A1 | 12/2002 | Schreck |
| 2003/0014104 A1 | 1/2003 | Cribier |
| 2003/0050694 A1 | 3/2003 | Yang et al. |
| 2003/0130729 A1 | 7/2003 | Paniagua et al. |
| 2003/0163194 A1 | 8/2003 | Quijano et al. |
| 2003/0167071 A1 | 9/2003 | Martin et al. |
| 2003/0171806 A1 | 9/2003 | Mathis et al. |
| 2003/0199975 A1 | 10/2003 | Gabbay |
| 2003/0229394 A1 | 12/2003 | Ogle et al. |
| 2003/0229395 A1 | 12/2003 | Cox |
| 2003/0233142 A1 | 12/2003 | Morales et al. |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015230 A1 | 1/2004 | Moll et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024451 A1 | 2/2004 | Johnson et al. |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0034411 A1 | 2/2004 | Quijano et al. |
| 2004/0039436 A1 | 2/2004 | Spenser et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0049266 A1 | 3/2004 | Anduiza et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0082991 A1 | 4/2004 | Nguyen et al. |
| 2004/0087975 A1 | 5/2004 | Lucatero et al. |
| 2004/0088045 A1 | 5/2004 | Cox |
| 2004/0088046 A1 | 5/2004 | Speziali |
| 2004/0092858 A1 | 5/2004 | Wilson et al. |
| 2004/0093060 A1 | 5/2004 | Sequin et al. |
| 2004/0093070 A1 | 5/2004 | Hojeibane et al. |
| 2004/0093080 A1 | 5/2004 | Helmus et al. |
| 2004/0097979 A1 | 5/2004 | Svanidze et al. |
| 2004/0098098 A1 | 5/2004 | McGuckin, Jr. et al. |
| 2004/0098112 A1 | 5/2004 | DiMatteo et al. |
| 2004/0102839 A1 | 5/2004 | Cohn et al. |
| 2004/0102840 A1 | 5/2004 | Solem et al. |
| 2004/0102842 A1 | 5/2004 | Jansen |
| 2004/0106976 A1 | 6/2004 | Bailey et al. |
| 2004/0106990 A1 | 6/2004 | Spence et al. |
| 2004/0106991 A1 | 6/2004 | Hopkins et al. |
| 2004/0111096 A1 | 6/2004 | Tu et al. |

| | | |
|---|---|---|
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138742 A1 | 7/2004 | Myers et al. |
| 2004/0138743 A1 | 7/2004 | Myers et al. |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153052 A1 | 8/2004 | Mathis |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |
| 2004/0186444 A1 | 9/2004 | Daly et al. |
| 2004/0186558 A1 | 9/2004 | Pavcnik et al. |
| 2004/0186561 A1 | 9/2004 | McGuckin, Jr. et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | McCarthy et al. |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Sequin et al. |
| 2004/0210305 A1 | 10/2004 | Shu et al. |
| 2004/0210306 A1 | 10/2004 | Quijano et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0220654 A1 | 11/2004 | Mathis et al. |
| 2004/0220657 A1 | 11/2004 | Nieminen et al. |
| 2004/0225322 A1 | 11/2004 | Garrison et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0230117 A1 | 11/2004 | Tosaya et al. |
| 2004/0230297 A1 | 11/2004 | Thornton |
| 2004/0236411 A1 | 11/2004 | Sarac et al. |
| 2004/0236418 A1 | 11/2004 | Stevens |
| 2004/0236419 A1 | 11/2004 | Milo |
| 2004/0243153 A1 | 12/2004 | Liddicoat et al. |
| 2004/0243219 A1 | 12/2004 | Fischer et al. |
| 2004/0243227 A1 | 12/2004 | Starksen et al. |
| 2004/0243228 A1 | 12/2004 | Kowalsky et al. |
| 2004/0243230 A1 | 12/2004 | Navia et al. |
| 2004/0254600 A1 | 12/2004 | Zarbatany et al. |
| 2004/0254636 A1 | 12/2004 | Flagle et al. |
| 2004/0260276 A1 | 12/2004 | Rudko et al. |
| 2004/0260317 A1 | 12/2004 | Bloom et al. |
| 2004/0260322 A1 | 12/2004 | Rudko et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0004583 A1 | 1/2005 | Oz et al. |
| 2005/0004667 A1 | 1/2005 | Swinford et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021056 A1 | 1/2005 | St. Goar et al. |
| 2005/0021136 A1 | 1/2005 | Xie et al. |
| 2005/0027261 A1 | 2/2005 | Wever et al. |
| 2005/0027348 A1 | 2/2005 | Case et al. |
| 2005/0027351 A1 | 2/2005 | Reuter et al. |
| 2005/0027353 A1 | 2/2005 | Alferness et al. |
| 2005/0033398 A1 | 2/2005 | Sequin |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0043790 A1 | 2/2005 | Seguin |
| 2005/0043792 A1 | 2/2005 | Solem et al. |
| 2005/0049679 A1 | 3/2005 | Taylor et al. |
| 2005/0049692 A1 | 3/2005 | Numamoto et al. |
| 2005/0049696 A1 | 3/2005 | Siess et al. |
| 2005/0049697 A1 | 3/2005 | Sievers |
| 2005/0054977 A1 | 3/2005 | Laird et al. |
| 2005/0055079 A1 | 3/2005 | Duran |
| 2005/0055087 A1 | 3/2005 | Starksen |
| 2005/0055088 A1 | 3/2005 | Liddicoat et al. |
| 2005/0055089 A1 | 3/2005 | Macoviak et al. |
| 2005/0060029 A1 | 3/2005 | Le et al. |
| 2005/0060030 A1 | 3/2005 | Lashinski et al. |
| 2005/0065460 A1 | 3/2005 | Laird |
| 2005/0065550 A1 | 3/2005 | Starksen et al. |
| 2005/0065594 A1 | 3/2005 | DiMatteo et al. |
| 2005/0065597 A1 | 3/2005 | Lansac |
| 2005/0070998 A1 | 3/2005 | Rourke et al. |
| 2005/0075584 A1 | 4/2005 | Cali |
| 2005/0075659 A1 | 4/2005 | Realyvasquez et al. |
| 2005/0075662 A1 | 4/2005 | Pedersen et al. |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075723 A1 | 4/2005 | Schroeder et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075729 A1 | 4/2005 | Nguyen et al. |
| 2005/0075730 A1 | 4/2005 | Myers et al. |
| 2005/0075731 A1* | 4/2005 | Artof et al. .................. 623/2.18 |
| 2005/0080483 A1 | 4/2005 | Solem et al. |
| 2005/0085900 A1 | 4/2005 | Case et al. |
| 2005/0085903 A1 | 4/2005 | Lau |
| 2005/0085904 A1 | 4/2005 | Lemmon |
| 2005/0090846 A1 | 4/2005 | Pedersen et al. |
| 2005/0096735 A1 | 5/2005 | Hojeibane et al. |
| 2005/0096738 A1 | 5/2005 | Cali et al. |
| 2005/0096739 A1 | 5/2005 | Cao |
| 2005/0096740 A1 | 5/2005 | Langberg et al. |
| 2005/0101975 A1 | 5/2005 | Nguyen et al. |
| 2005/0102026 A1 | 5/2005 | Turner et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107872 A1 | 5/2005 | Mensah et al. |
| 2005/0113910 A1 | 5/2005 | Paniagua et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0137449 A1 | 6/2005 | Nieminen et al. |
| 2005/0137450 A1 | 6/2005 | Aronson et al. |

| | | | | | |
|---|---|---|---|---|---|
| 2005/0137451 A1 | 6/2005 | Gordon et al. | 2005/0267565 A1 | 12/2005 | Dave et al. |
| 2005/0137676 A1 | 6/2005 | Richardson et al. | 2005/0267571 A1 | 12/2005 | Spence et al. |
| 2005/0137681 A1 | 6/2005 | Shoemaker et al. | 2005/0267573 A9 | 12/2005 | Macoviak et al. |
| 2005/0137682 A1 | 6/2005 | Justino | 2005/0267574 A1 | 12/2005 | Cohn et al. |
| 2005/0137685 A1 | 6/2005 | Nieminen et al. | 2005/0272969 A1 | 12/2005 | Alferness et al. |
| 2005/0137686 A1 | 6/2005 | Salahieh et al. | 2005/0273160 A1 | 12/2005 | Lashinski et al. |
| 2005/0137688 A1 | 6/2005 | Salahieh et al. | 2005/0278015 A1 | 12/2005 | Dave et al. |
| 2005/0137689 A1 | 6/2005 | Salahieh et al. | 2005/0283178 A1 | 12/2005 | Flagle et al. |
| 2005/0137690 A1 | 6/2005 | Salahieh et al. | 2005/0283231 A1* | 12/2005 | Haug et al. .................. 623/2.11 |
| 2005/0137691 A1 | 6/2005 | Salahieh et al. | 2005/0288779 A1 | 12/2005 | Shaoulian et al. |
| 2005/0137692 A1 | 6/2005 | Haug et al. | 2006/0000715 A1 | 1/2006 | Whitcher et al. |
| 2005/0137693 A1 | 6/2005 | Haug et al. | 2006/0004439 A1 | 1/2006 | Spenser et al. |
| 2005/0137694 A1 | 6/2005 | Haug et al. | 2006/0004442 A1 | 1/2006 | Spenser et al. |
| 2005/0137696 A1 | 6/2005 | Salahieh et al. | 2006/0009841 A1 | 1/2006 | McGuckin et al. |
| 2005/0137697 A1 | 6/2005 | Salahieh et al. | 2006/0009842 A1 | 1/2006 | Huynh et al. |
| 2005/0137698 A1 | 6/2005 | Salahieh et al. | 2006/0013805 A1 | 1/2006 | Hebbel et al. |
| 2005/0137699 A1 | 6/2005 | Salahieh et al. | 2006/0013855 A1 | 1/2006 | Carpenter et al. |
| 2005/0137700 A1 | 6/2005 | Spence et al. | 2006/0015136 A1 | 1/2006 | Besselink |
| 2005/0137701 A1 | 6/2005 | Salahieh et al. | 2006/0015178 A1 | 1/2006 | Moaddeb et al. |
| 2005/0137702 A1 | 6/2005 | Haug et al. | 2006/0015179 A1 | 1/2006 | Bulman-Fleming et al. |
| 2005/0143807 A1 | 6/2005 | Pavcnik et al. | 2006/0020275 A1 | 1/2006 | Goldfarb et al. |
| 2005/0143809 A1 | 6/2005 | Salahieh et al. | 2006/0020327 A1 | 1/2006 | Lashinski et al. |
| 2005/0143810 A1 | 6/2005 | Dauner et al. | 2006/0020332 A1 | 1/2006 | Lashinski et al. |
| 2005/0143811 A1 | 6/2005 | Realyvasquez | 2006/0020334 A1 | 1/2006 | Lashinski et al. |
| 2005/0149014 A1 | 7/2005 | Hauck et al. | 2006/0020335 A1 | 1/2006 | Kowalsky et al. |
| 2005/0149179 A1 | 7/2005 | Mathis et al. | 2006/0020336 A1 | 1/2006 | Liddicoat |
| 2005/0149180 A1 | 7/2005 | Mathis et al. | 2006/0025750 A1 | 2/2006 | Starksen et al. |
| 2005/0149181 A1 | 7/2005 | Eberhardt | 2006/0025784 A1 | 2/2006 | Starksen et al. |
| 2005/0159810 A1 | 7/2005 | Filsoufi | 2006/0025787 A1 | 2/2006 | Morales et al. |
| 2005/0159811 A1 | 7/2005 | Lane | 2006/0025854 A1 | 2/2006 | Lashinski et al. |
| 2005/0165477 A1 | 7/2005 | Anduiza et al. | 2006/0025855 A1 | 2/2006 | Lashinski et al. |
| 2005/0165478 A1 | 7/2005 | Song | 2006/0025856 A1 | 2/2006 | Ryan et al. |
| 2005/0171472 A1 | 8/2005 | Lutter | 2006/0025857 A1 | 2/2006 | Bergheim et al. |
| 2005/0171601 A1 | 8/2005 | Cosgrove et al. | 2006/0030747 A1 | 2/2006 | Kantrowitz et al. |
| 2005/0177227 A1 | 8/2005 | Heim et al. | 2006/0030866 A1 | 2/2006 | Schreck |
| 2005/0177228 A1 | 8/2005 | Solem et al. | 2006/0030882 A1 | 2/2006 | Adams et al. |
| 2005/0182483 A1 | 8/2005 | Osborne et al. | 2006/0030885 A1 | 2/2006 | Hyde |
| 2005/0184122 A1 | 8/2005 | Hlavka et al. | 2006/0036317 A1 | 2/2006 | Vidlund et al. |
| 2005/0187614 A1 | 8/2005 | Agnew | 2006/0041305 A1 | 2/2006 | Lauterjung |
| 2005/0187616 A1 | 8/2005 | Realyvasquez | 2006/0041306 A1 | 2/2006 | Vidlund et al. |
| 2005/0187617 A1 | 8/2005 | Navia | 2006/0047297 A1 | 3/2006 | Case |
| 2005/0192606 A1 | 9/2005 | Paul, Jr. et al. | 2006/0047338 A1 | 3/2006 | Jenson |
| 2005/0192665 A1 | 9/2005 | Spenser et al. | 2006/0047343 A1 | 3/2006 | Oviatt et al. |
| 2005/0197692 A1 | 9/2005 | Pai et al. | 2006/0052804 A1 | 3/2006 | Mialhe |
| 2005/0197693 A1 | 9/2005 | Pai et al. | 2006/0052867 A1 | 3/2006 | Revuelta et al. |
| 2005/0197694 A1 | 9/2005 | Pai et al. | 2006/0058817 A1 | 3/2006 | Starksen et al. |
| 2005/0203549 A1 | 9/2005 | Realyvasquez | 2006/0058865 A1 | 3/2006 | Case et al. |
| 2005/0203605 A1 | 9/2005 | Dolan | 2006/0058871 A1 | 3/2006 | Zakey et al. |
| 2005/0203614 A1 | 9/2005 | Forster et al. | 2006/0058889 A1 | 3/2006 | Case et al. |
| 2005/0203615 A1 | 9/2005 | Forster et al. | 2006/0064115 A1 | 3/2006 | Allen et al. |
| 2005/0203616 A1 | 9/2005 | Cribier | 2006/0064116 A1 | 3/2006 | Allen et al. |
| 2005/0203617 A1 | 9/2005 | Forster et al. | 2006/0064118 A1 | 3/2006 | Kimblad |
| 2005/0203618 A1 | 9/2005 | Sharkawy et al. | 2006/0064174 A1 | 3/2006 | Zadno |
| 2005/0216039 A1 | 9/2005 | Lederman | 2006/0069400 A1 | 3/2006 | Burnett et al. |
| 2005/0216077 A1 | 9/2005 | Mathis et al. | 2006/0069430 A9 | 3/2006 | Rahdert et al. |
| 2005/0216078 A1 | 9/2005 | Starksen et al. | 2006/0074483 A1 | 4/2006 | Schrayer |
| 2005/0222675 A1 | 10/2005 | Sauter | 2006/0074484 A1 | 4/2006 | Huber |
| 2005/0222678 A1 | 10/2005 | Lashinski et al. | 2006/0074485 A1 | 4/2006 | Realyvasquez |
| 2005/0228422 A1 | 10/2005 | Machold et al. | 2006/0085060 A1 | 4/2006 | Campbell |
| 2005/0228479 A1 | 10/2005 | Pavenik et al. | 2006/0089708 A1 | 4/2006 | Osse et al. |
| 2005/0228486 A1 | 10/2005 | Case et al. | 2006/0095115 A1 | 5/2006 | Bladillah et al. |
| 2005/0228494 A1 | 10/2005 | Marquez | 2006/0095125 A1 | 5/2006 | Chinn et al. |
| 2005/0228495 A1 | 10/2005 | Macoviak | 2006/0099326 A1 | 5/2006 | Keogh et al. |
| 2005/0228496 A1 | 10/2005 | Mensah et al. | 2006/0100697 A1 | 5/2006 | Casanova |
| 2005/0234541 A1 | 10/2005 | Hunt et al. | 2006/0100699 A1 | 5/2006 | Vidlund et al. |
| 2005/0234546 A1 | 10/2005 | Nugent et al. | 2006/0106278 A1 | 5/2006 | Machold et al. |
| 2005/0240200 A1 | 10/2005 | Bergheim | 2006/0106279 A1 | 5/2006 | Machold et al. |
| 2005/0240202 A1 | 10/2005 | Shennib et al. | 2006/0106456 A9 | 5/2006 | Machold et al. |
| 2005/0240255 A1 | 10/2005 | Schaeffer | 2006/0111660 A1 | 5/2006 | Wolf et al. |
| 2005/0240259 A1 | 10/2005 | Sisken et al. | 2006/0111773 A1 | 5/2006 | Rittgers et al. |
| 2005/0240262 A1 | 10/2005 | White | 2006/0111774 A1 | 5/2006 | Samkov et al. |
| 2005/0244460 A1 | 11/2005 | Alferiev et al. | 2006/0116572 A1 | 6/2006 | Case |
| 2005/0246013 A1 | 11/2005 | Gabbay | 2006/0116756 A1 | 6/2006 | Solem et al. |
| 2005/0251251 A1 | 11/2005 | Cribler | 2006/0122686 A1 | 6/2006 | Gilad et al. |
| 2005/0256566 A1 | 11/2005 | Gabbay | 2006/0122692 A1 | 6/2006 | Gilad et al. |
| 2005/0261704 A1 | 11/2005 | Mathis | 2006/0122693 A1 | 6/2006 | Biadillah et al. |
| 2005/0261759 A1 | 11/2005 | Lambrecht et al. | 2006/0127443 A1 | 6/2006 | Helmus |
| 2005/0267493 A1 | 12/2005 | Schreck et al. | 2006/0129235 A1 | 6/2006 | Sequin et al. |
| 2005/0267560 A1 | 12/2005 | Bates | 2006/0129236 A1 | 6/2006 | McCarthy |

| | | | | | | |
|---|---|---|---|---|---|---|
| 2006/0135476 | A1 | 6/2006 | Kutryk et al. | WO | 2004091449 | 10/2004 |
| 2006/0135964 | A1 | 6/2006 | Vesley | WO | 2004091454 | 10/2004 |
| 2006/0135967 | A1 | 6/2006 | Realyvasquez | WO | 2004093638 | 11/2004 |
| 2006/0136044 | A1 | 6/2006 | Osborne et al. | WO | 2004093726 | 11/2004 |
| 2006/0136045 | A1 | 6/2006 | Flagle et al. | WO | 2004093728 | 11/2004 |
| 2006/0136052 | A1 | 6/2006 | Vesley | WO | 2004093730 | 11/2004 |
| 2006/0136054 | A1 | 6/2006 | Berg et al. | WO | 2004093745 | 11/2004 |
| 2006/0142846 | A1 | 6/2006 | Pavcnik et al. | WO | 2004093935 | 11/2004 |
| 2006/0142847 | A1 | 6/2006 | Shaknovich | WO | 2004096100 | 11/2004 |
| 2006/0142848 | A1 | 6/2006 | Gabbay | WO | 2004103222 | 12/2004 |
| 2006/0142854 | A1 | 6/2006 | Alferness et al. | WO | 2004103223 | 12/2004 |
| 2006/0149358 | A1 | 7/2006 | Zilla et al. | WO | 2004105584 | 12/2004 |
| 2006/0149360 | A1 | 7/2006 | Schwammenthal et al. | WO | 2004105651 | 12/2004 |
| 2006/0149367 | A1 | 7/2006 | Sieracki | WO | 2004112582 | 12/2004 |
| 2006/0149368 | A1 | 7/2006 | Spence | WO | 2004112585 | 12/2004 |
| 2006/0161133 | A1 | 7/2006 | Laird et al. | WO | 2004112643 | 12/2004 |
| 2006/0161248 | A1 | 7/2006 | Case et al. | WO | 2004112652 | 12/2004 |
| 2006/0161250 | A1 | 7/2006 | Shaw | WO | 2004112657 | 12/2004 |
| 2006/0167468 | A1 | 7/2006 | Gabbay | WO | 2004112658 | 12/2004 |
| 2006/0167541 | A1 | 7/2006 | Lattouf | WO | 2005000152 | 1/2005 |
| 2006/0167542 | A1 | 7/2006 | Quintessenza | WO | 2005002424 | 1/2005 |
| 2006/0167543 | A1 | 7/2006 | Bailey et al. | WO | 2005002466 | 1/2005 |
| 2006/0195180 | A1 | 8/2006 | Kheradvar et al. | WO | 2005004753 | 1/2005 |
| | | | | WO | 2005007017 | 1/2005 |
| | FOREIGN PATENT DOCUMENTS | | | WO | 2005007018 | 1/2005 |
| | | | | WO | 2005007036 | 1/2005 |
| EP | 0 466 518 | | 1/1992 | WO | 2005007037 | 1/2005 |
| FR | 2 728 457 | | 6/1996 | WO | 2005009285 | 2/2005 |
| WO | 8800459 | | 1/1988 | WO | 2005009286 | 2/2005 |
| WO | 9015582 | | 12/1990 | WO | 2005009505 | 2/2005 |
| WO | 9501669 | | 1/1995 | WO | 2005009506 | 2/2005 |
| WO | 9619159 | | 6/1996 | WO | 2005011473 | 2/2005 |
| WO | 9803656 | | 1/1998 | WO | 2005011534 | 2/2005 |
| WO | 9846115 | | 10/1998 | WO | 2005011535 | 2/2005 |
| WO | 9904724 | | 2/1999 | WO | 2005013860 | 2/2005 |
| WO | WO 00/47139 | | 8/2000 | WO | 2005018507 | 3/2005 |
| WO | 0067679 | | 11/2000 | WO | 2005021063 | 3/2005 |
| WO | 0115650 | | 3/2001 | WO | 2005023155 | 3/2005 |
| WO | 0117462 | | 3/2001 | WO | 2005025644 | 3/2005 |
| WO | WO 01/54624 A1 | | 8/2001 | WO | 2005027790 | 3/2005 |
| WO | 03047468 | | 6/2003 | WO | 2005027797 | 3/2005 |
| WO | 03084443 | | 10/2003 | WO | 2005034812 | 4/2005 |
| WO | 2004019825 | | 3/2004 | WO | 2005039428 | 5/2005 |
| WO | 2004021893 | | 3/2004 | WO | 2005039452 | 5/2005 |
| WO | 2004023980 | | 3/2004 | WO | 2005046488 | 5/2005 |
| WO | 2004030568 | | 4/2004 | WO | 2005046528 | 5/2005 |
| WO | 2004030569 | | 4/2004 | WO | 2005046529 | 5/2005 |
| WO | 2004030570 | | 4/2004 | WO | 2005046530 | 5/2005 |
| WO | 2004032724 | | 4/2004 | WO | 2005046531 | 5/2005 |
| WO | 2004032796 | | 4/2004 | WO | 2005048883 | 6/2005 |
| WO | 2004037128 | | 5/2004 | WO | 2005049103 | 6/2005 |
| WO | 2004037317 | | 5/2004 | WO | 2005051226 | 6/2005 |
| WO | 2004039432 | | 5/2004 | WO | 2005055811 | 6/2005 |
| WO | 2004043265 | | 5/2004 | WO | 2005055883 | 6/2005 |
| WO | 2004043273 | | 5/2004 | WO | 2005058206 | 6/2005 |
| WO | 2004043293 | | 5/2004 | WO | 2005065585 | 7/2005 |
| WO | 2004045370 | | 6/2004 | WO | 2005065593 | 7/2005 |
| WO | 2004045378 | | 6/2004 | WO | 2005065594 | 7/2005 |
| WO | 2004045463 | | 6/2004 | WO | 2005070342 | 8/2005 |
| WO | 2004047677 | | 6/2004 | WO | 2005070343 | 8/2005 |
| WO | 2004060217 | | 7/2004 | WO | 2005072654 | 8/2005 |
| WO | 2004060470 | | 7/2004 | WO | 2005072655 | 8/2005 |
| WO | 2004062725 | | 7/2004 | WO | 2005079706 | 9/2005 |
| WO | 2004060826 | | 8/2004 | WO | 2005082288 | 9/2005 |
| WO | 2004066803 | | 8/2004 | WO | 2005082289 | 9/2005 |
| WO | 2004069287 | | 8/2004 | WO | 2005084595 | 9/2005 |
| WO | 2004075789 | | 9/2004 | WO | 2005087139 | 9/2005 |
| WO | 2004080352 | | 9/2004 | WO | 2005087140 | 9/2005 |
| WO | 2004082523 | | 9/2004 | WO | 2006000090 | 1/2006 |
| WO | 2004082527 | | 9/2004 | WO | 2006000763 | 1/2006 |
| WO | 2004082528 | | 9/2004 | WO | 2006000776 | 1/2006 |
| WO | 2004082536 | | 9/2004 | WO | 2006002492 | 1/2006 |
| WO | 2004082537 | | 9/2004 | WO | 2006004679 | 1/2006 |
| WO | 2004082538 | | 9/2004 | WO | 2006005015 | 1/2006 |
| WO | 2004082757 | | 9/2004 | WO | 2006011127 | 2/2006 |
| WO | 2004084746 | | 10/2004 | WO | 2006012011 | 2/2006 |
| WO | 2004084770 | | 10/2004 | WO | 2006012013 | 2/2006 |
| WO | 2004089246 | | 10/2004 | WO | 2006012038 | 2/2006 |
| WO | 2004089250 | | 10/2004 | WO | 2006012068 | 2/2006 |
| WO | 2004089253 | | 10/2004 | | | |

| | | |
|---|---|---|
| WO | 2006012322 | 2/2006 |
| WO | 2006019498 | 2/2006 |
| WO | 2006026371 | 3/2006 |
| WO | 2006026377 | 3/2006 |
| WO | 2006026912 | 3/2006 |
| WO | 2006027499 | 3/2006 |
| WO | 2006028821 | 3/2006 |
| WO | 2006029062 | 3/2006 |
| WO | 2006031436 | 3/2006 |
| WO | 2006031469 | 3/2006 |
| WO | 2006032051 | 3/2006 |
| WO | 2006034245 | 3/2006 |
| WO | 2006035415 | 4/2006 |
| WO | 2006041505 | 4/2006 |
| WO | 2006044679 | 4/2006 |
| WO | 2006048664 | 5/2006 |
| WO | 2006050459 | 5/2006 |
| WO | 2006050460 | 5/2006 |
| WO | 2006054107 | 5/2006 |
| WO | 2006054930 | 5/2006 |
| WO | 2006055982 | 5/2006 |
| WO | 2006060546 | 6/2006 |
| WO | 2006063108 | 6/2006 |
| WO | 2006063181 | 6/2006 |
| WO | 2006063199 | 6/2006 |
| WO | 2006064490 | 6/2006 |
| WO | 2006065212 | 6/2006 |
| WO | 2006065930 | 6/2006 |
| WO | 2006066148 | 6/2006 |
| WO | 2006066150 | 6/2006 |
| WO | 2006069094 | 6/2006 |
| WO | 2006070372 | 7/2006 |
| WO | 2006073628 | 7/2006 |
| WO | 2006076890 | 7/2006 |

OTHER PUBLICATIONS

PCT International Preliminary Report on Patentability.

* cited by examiner

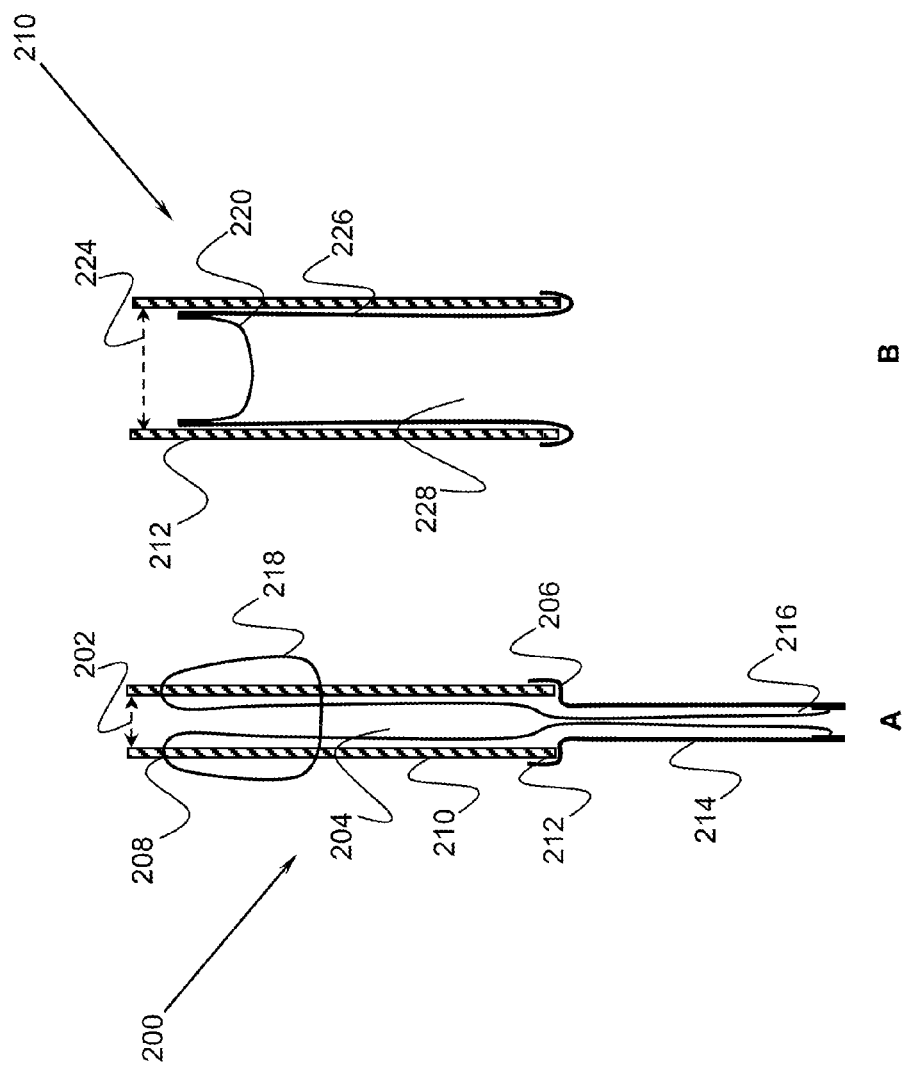

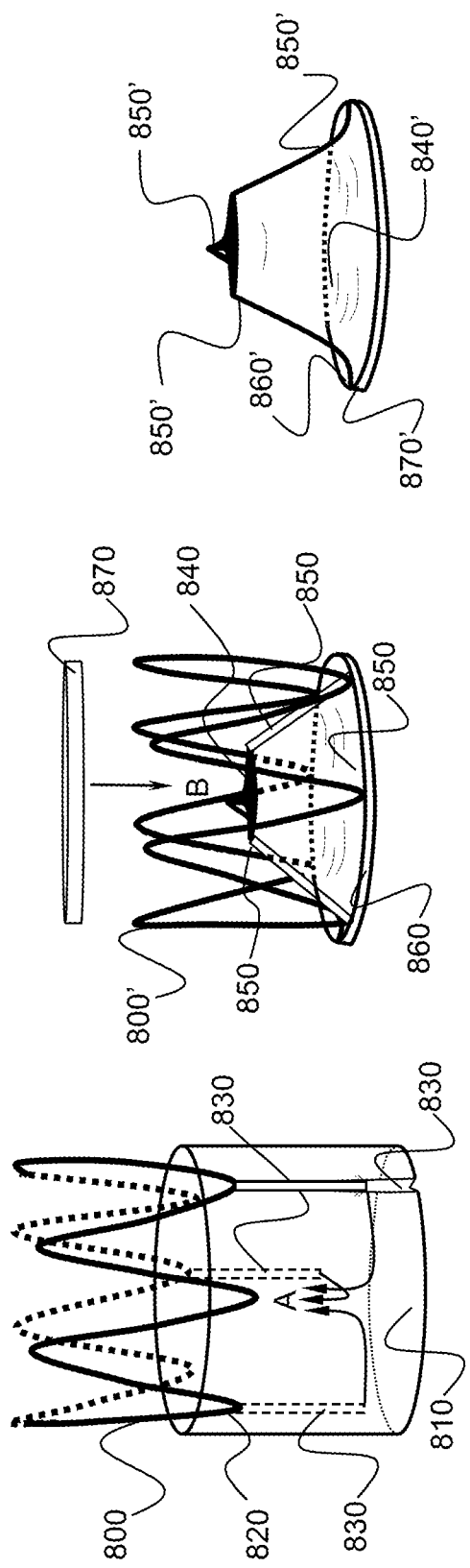

IN-SITU FORMATION OF A VALVE

PRIORITY CLAIM

The present application is a non-provisional patent application, claiming the benefit of priority of U.S. Provisional Patent Application No. 60/879,288, filed Jan. 8, 2007, titled, "In-situ formation of a valve by infolding leaflets and its method of delivery;" and U.S. Provisional Patent Application No. 60/930,458, filed May 16, 2007, titled, "Deployable forming heart valve system and its percutaneous method of delivery."

BACKGROUND OF THE INVENTION (1) Technical Field

The present invention is related to a prosthetic valve and a method for implantation in a body channel, and methods of delivery.

(2) Description of Related Art

Human heart valves under the conditions of normal physiological functions are organs that open under the changes in pressure gradient inside the cardiac chambers. Four valves in the heart serve to direct the flow of blood through all chambers in a forward direction. In addition to the four heart valves (tricuspid valve, mitral valve, aortic valve, and pulmonary valve), a patient has other flow-regulatory valves, such as venous valves, sphincter valves, and the like.

When disease conditions affect the structure or the materials of the native valve, the valve itself will decay, degenerate or disrupt and requires repair or replacement to restore proper function necessary for the continuation of life.

U.S. Pat. No. 4,451,936 to Carpentier et al., entire contents of which are incorporated herein by reference, discloses an aortic prosthetic valve for supra-annular implantation comprising a valve body of generally annular configuration and a valve element movably mounted on the valve body for opening and closing the valve, and a scalloped suture ring circumscribing the valve body adjacent the base surface and configured to approximately fit the contour of the Sinuses of Valsalva at the base of the aorta.

U.S. Pat. No. 4,790,843 to Carpentier et al., entire contents of which are incorporated herein by reference, discloses a prosthetic heart valve assembly that includes an artificial annulus, a prosthetic valve and a retaining ring for releasably retaining the prosthetic valve on the artificial annulus. By removing the retaining ring, the valve can be replaced with another valve.

U.S. Pat. No. 4,994,077 to Gabbay, entire contents of which are incorporated herein by reference, discloses an improved prosthetic heart valve comprising a support body or stent covered by a layer of biological tissue having only the smooth surfaces thereof presented outwardly. The valve cusp is made of pericardial tissue that has been doubled over such that the rough side thereof is folded inwardly.

U.S. Pat. No. 4,994,077 to Dobben, entire contents of which are incorporated herein by reference, discloses a valve system consisting of a cylindrical or crown shaped stent that is made by bending wire into a zigzag shape to anchor the device and attach the flow regulator flap of a valve. The device presents significant hemodynamic, delivery, fatigue and stability disadvantages.

U.S. Pat. No. 5,163,953 to Vince, entire contents of which are incorporated herein by reference, discloses a valve system consisting of a flow-regulation mechanism of a flap of biologic material that is mounted inside a stent comprised of a toroidal body formed of a flexible coil of wire. The main shortcoming of this design is the profile and configuration, thus making the device clinically ineffective as a minimally invasive technique.

U.S. Pat. No. 5,332,402 to Teitelbaum, entire contents of which are incorporated herein by reference, discloses a valve system consisting of shape memory Nitinol and a flow-regulating valve. The stent-like support is comprised of a meshwork or braiding of Nitinol wire with trumpet-like distal and proximal flares. The flared ends are intended to maintain the position of the stent component across the valve thereby anchoring the device. The disadvantages of the device are the reduced valve orifice and sub-optimal hemodynamic characteristics.

U.S. Pat. No. 5,370,685 to Stevens, entire contents of which are incorporated herein by reference, discloses a percutaneous valve replacement system for the endovascular removal of a malfunctioning valve followed by replacement with a prosthetic valve. The valve replacement system may include a prosthetic valve device comprised of a stent and cusps for flow-regulation such as a fixed porcine aortic valve, a valve introducer, an intraluminal procedure device, a procedure device capsule and a tissue cutter. The valve device disclosed requires a large delivery catheter and intraluminal-securing means such as suturing to anchor the device at the desired location.

U.S. Pat. No. 5,397,351 to Pavcnik et al., entire contents of which are incorporated herein by reference, discloses a self-expanding percutaneous valve comprised of a poppet, a stent and a restraining element. The valve stent has barbed means to anchor to the internal passageway. The device includes a self-expanding stent of a zigzag configuration in conjunction with a cage mechanism comprised of a multiplicity of criss-crossed wires and a valve seat. The disadvantages of the device include large delivery profile, reduced effective valvular orifice, and possible perivalvular leakage.

U.S. Pat. No. 5,411,552 to Andersen et al., entire contents of which are incorporated herein by reference, discloses various balloon expandable percutaneous prosthetic valves. One embodiment discloses a valve prosthesis comprised of a stent made from an expandable cylindrical structure and an elastically collapsible valve mounted to the stent. The device is placed at the desired location by balloon expanding the stent and the valve. The main disadvantage to this design is the 20+ French size delivery catheters.

U.S. Pat. No. 5,445,626 to Gigante, entire contents of which are incorporated herein by reference, discloses a valve operated catheter for urinary incontinence and retention comprising a flexible duct designed to be inserted in the patient's urethra, the catheter provided with a spiral shaped end portion, having a plurality of holes for the passage of urine. The duct is provided, at its other end, with a seat in which there is housed a valve made of elastic material, the valve being usually closed because of the elastic action.

U.S. Pat. No. 5,500,014 to Quijano et al., entire contents of which are incorporated herein by reference, discloses a biological valvular prosthesis comprising a chemically fixed conduit derived from a harvested vein segment bearing at least one integrally formed venous valve, and a restriction means positioned about the conduit at either side of the venous for restricting the venous valve from expanding outwardly.

U.S. Pat. No. 5,824,064 to Taheri, entire contents of which are incorporated herein by reference, discloses an aortic valve replacement system combined with an aortic arch graft. The devices and percutaneous methods described require puncture of the chest cavity.

U.S. Pat. No. 5,840,081 to Andersen et al., entire contents of which are incorporated herein by reference, discloses a valve prosthesis for implantation in the body by use of a catheter. The valve prosthesis is formed of a stent with a pre-formed collapsible valve mounted on the stent.

U.S. Pat. No. 5,855,597 to Jayaraman, entire contents of which are incorporated herein by reference, discloses a device comprising a star-shaped stent, a replacement valve and a replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner.

U.S. Pat. No. 5,855,601 to Bessler et al., entire contents of which are incorporated herein by reference, discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire in a zigzag configuration that can be a single piece, stamped, extruded or formed by welding the free ends together. The flow-regulation mechanism is comprised of an arcuate portion that contains a slit to form leaflets and a cuff portion that is sutured to the stent and encloses the stent. The preferred flow regulator is a porcine pericardium with three cusps.

U.S. Pat. No. 5,925,063 to Khosravi, entire contents of which are incorporated herein by reference, discloses a percutaneous prosthetic valve comprised of a coiled sheet stent to which a plurality of flaps are mounted on the interior surface to form a flow-regulation mechanism that may be comprised of a biocompatible material. The disadvantages of this design include problematic interactions between the stent and flaps in the delivery state, and the lack of a detailed mechanism to ensure that the flaps will create a competent one-directional valve.

U.S. Pat. No. 5,954,766 to Zadano-Azizi et al., entire contents of which are incorporated herein by reference, discloses a device in which flow-regulation is provided by a flap disposed within a frame structure capable of taking an insertion state and an expanded state. The preferred embodiment of the flow-regulation mechanism is defined by a longitudinal valve body made of a sufficiently resilient material with a slit that extends longitudinally through the valve body.

U.S. Pat. No. 5,957,949 to Leonhardt et al., entire contents of which are incorporated herein by reference, discloses a prosthetic valve comprised of a tubular graft having radially compressible annular spring portions and a flow regulator, which is preferably a biological valve disposed within. In addition to oversizing the spring stent by 30%, anchoring means is provided by a light-activated biocompatible tissue adhesive that is located on the outside of the tubular graft and seals to the living tissue. Disadvantages of this device include those profile concerns, a large diameter complex delivery system, and feasibility of the light actuated anchoring means.

U.S. Pat. No. 6,106,550 to Magovern et al., entire contents of which are incorporated herein by reference, discloses an implantable apparatus for receiving a heart valve, comprising an annular ring having an inner wall and an outer wall, a plurality of channels displaced circumferentially about the ring, each channel extending from the inner wall to the outer wall, and a plurality of tissue attachment pins each pin being movable in a respective one of the channels between a first position during implantation, and a second position wherein the first end of each pin extends beyond the outer wall for tissue attachment.

U.S. Pat. No. 6,168,614 to Andersen et al., entire contents of which are incorporated herein by reference, discloses a method of endovascularly delivering a valve through a blood vessel, comprising the steps of providing a tissue valve and an expandable support structure, connecting the tissue valve to the support structure, and securing the tissue valve and the support structure to a desired valve location with the support structure in the expanded shape.

U.S. Pat. No. 6,206,911 to Milo, entire contents of which are incorporated herein by reference, discloses an expandable stent that is created so as to undergo essentially no axial foreshortening when expanded from an unexpanded or compressed configuration to an operative configuration. Attachment to the surrounding tissue may be via pairs of needle-like projections or prongs that may be bent to have a radial orientation during the deployment phase.

U.S. Pat. No. 6,283,127 to Sterman et al., entire contents of which are incorporated herein by reference, discloses a device system and methods facilitating intervention within the heart or a great vessel without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum.

U.S. Pat. No. 6,530,952 to Vesely, entire contents of which are incorporated herein by reference, discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing whereas a new collapsible valve is then installed, to resume the function of the prosthesis.

U.S. Pat. No. 6,569,196 to Vesely, entire contents of which are incorporated herein by reference, discloses a system for minimally invasive insertion of a bioprosthetic heart valve. The system includes a collapsible tissue-based valve system, a catheter-based valve delivery system, a surgical platform and a device tracking and visualization system, wherein the collapsible valve system includes a permanent outer frame that is affixed to the patient using conventional sutures or staples and a collapsible valve having a collapsible inner frame that mates with the outer frame.

U.S. Pat. No. 6,582,462 to Andersen et al., entire contents of which are incorporated herein by reference, discloses a valve prosthesis for implantation in a body channel by way of catheterization, the prosthesis comprising a radially collapsible and expandable cylindrical stent and a collapsible and expandable valve having commissural points wherein the valve is mounted to the stent at the commissural points.

U.S. Pat. No. 6,652,578 to Bailey et al., entire contents of which are incorporated herein by reference, discloses a catheter system with minimally invasive techniques for percutaneous and transluminal valvuloplasty and prosthetic valve implantation.

U.S. Pat. No. 6,830,584 to Seguin, entire contents of which are incorporated herein by reference, discloses a device for replacing, via a percutaneous route, a heart valve located in a bodily vessel, comprising an elongated support element, two series of elongated blades arranged around the circumference of the elongated elements, where the blades have opposite cutting edges and can be extended corolla-shaped such that their cutting edges are set in the extension of one another thereby forming circular cutting edges to cut the native valve so as to separate it from the corporeal duct.

U.S. Pat. No. 6,830,585 to Artof et al., entire contents of which are incorporated herein by reference, discloses a percutaneously deliverable heart valve with a plurality of valvular leaflets, the plurality of leaflets being sewn together at least a portion of their side edges to form an annulus at about the in-flow edge and a plurality of commissure tissues.

U.S. Pat. No. 6,896,690 to Lambrecht et al., entire contents of which are incorporated herein by reference, discloses a device for performing intravascular procedures wherein at least a portion of the device is configured for placement in a flowpath of a blood vessel. The device comprises a valve means configured to allow greater antegrade flow than retrograde flow through the vessel and a filter operative to restrict the passage of emboli while allowing blood flow through the vessel.

U.S. Pat. No. 6,908,481 to Cribier, entire contents of which are incorporated herein by reference, discloses a valve prosthesis comprising a collapsible, elastic valve member, an elastic stent member in which the valve member is mounted, and a support coupled to the valve member and positioned between the valve member and the stent member, wherein the stent member forms a continuous surface and comprises strut members that provide a structure sufficiently rigid to prevent eversion.

U.S. Pat. No. 6,951,571 to Srivastava, entire contents of which are incorporated herein by reference, discloses a valve-implanting device comprising a collapsible frame, inner and outer guide wires removably connected to the collapsible frame, and a plurality of valve flaps attached to the collapsible frame.

U.S. Pat. No. 6,974,476 to McGuckin, Jr. et al., entire contents of which are incorporated herein by reference, discloses a valve system comprising a first substantially annular portion adapted to be positioned on a proximal side of the annulus of a patient and a second substantially annular portion adapted to be positioned on a distal side of the annulus of a patient, wherein at least one of the first and second substantially annular portions is movable towards the other portion to a clamped position to clamp around the annulus. The second portion has a flow restricting apparatus.

Each of the prior art stent valve designs has certain disadvantages which are resolved by the present embodiments. The prior art valve prosthesis generally consists of a support structure with a tissue valve connected to it, wherein the support structure is delivered in a collapsed shape intraluminally and secured to a desired valve location with the support structure in the expanded shape. However, the support structure tends to compressively impinge a portion of the leaflets of the tissue valve at the structure struts when the support structure is expanded by an inflatable balloon for positioning endovascularly. The impinged leaflets tend to deteriorate and calcify, making the valve useless. Moreover, recent studies showed that there is an imperfect apposition of the stent against the native valve which resulted in paravalvular leak and obstruction of coronary Ostia at the coronary sinuses. Additionally, existing stent designs set a limit for a minimum catheter size and cannot be delivered with small enough catheters. As a result, one direct disadvantage of the size limitation is the exclusion of children from the beneficiaries of this technology. Thus, a continuing need exists for a new and improved expanding valve structure that is formed in-situ and that can be used with tiny catheters.

SUMMARY OF THE INVENTION

It is an objective of the present invention to provide a valve prosthesis which is formed in situ. It is also an objective of the present invention to permit implantation of the prosthetic valve without surgical intervention in the body.

In one aspect the present invention is an in-situ forming valve, comprising: an expandable component comprising a hollow portion, a distal end, and a proximal end; a sheet component comprising a distal circumference and a proximal circumference, the distal circumference held in at least partial contact with the distal end of the expandable component, the proximal end of the sheet component further comprising at least two pinched regions; and an at least one link detachably attached to at least one point of the proximal end of the sheet, the link configured to position the proximal end of the sheet component into the hollow portion of the expandable component thereby forming a functional valve in situ.

In another aspect of the present invention, the sheet component comprises a single tubular sheet.

In another aspect of the present invention, the sheet component is a multitude of sheet components sealed together.

In another aspect of the present invention, the at least one link is further attached to at least one point above the distal end of the expandable component such that the expansion of the expandable component is configured to position the proximal end of the sheet component into the hollow portion of the expandable component thereby forming a functional valve in situ.

In another aspect of the present invention, the expandable component is at least partially comprised of a shape memory material.

In another aspect of the present invention, the expandable component is at least partially comprised of an elastic material.

In another aspect of the present invention, the expandable component is equipped with at least one bioactive agent selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, platelet aggregation inhibitor agents, antibacterial agents, antiviral agents, antimicrobials, and anti-infectives.

In yet another aspect of the present invention, the sheet component is made from a material selected from a group consisting of natural membranes, synthetic material, engineered biological tissue, biological valvular leaflet tissue, pericardial tissue, and cross-linked pericardial tissue.

In another aspect of the present invention, the invention further comprises an elongate delivery apparatus, wherein the in-situ formed valve is collapsibly mounted onto the elongate delivery apparatus.

In another aspect of the present invention, the distal end of the at least one hollow sheet component at least partially extends out from the hollow portion and over the distal end of the expandable component.

In another aspect of the present invention, the at least one link is detachably attached to at least three points of contact along the proximal end of the sheet, the link configured to position the proximal end of the sheet component into the hollow portion of the expandable component, thereby forming a three flap valve in situ.

In another aspect of the present invention, the at least one link is made of a dissolvable material.

In a still further aspect of the present invention, the invention is an in-situ forming valve, comprising: an expandable component comprising a hollow portion, a distal end, and a proximal end; and a sheet component at least partially enveloping the distal end of the expandable component, the sheet component having a first pre-implantation configuration and a second functional valvular configuration, the first pre-implantation configuration is configured to transform to the second functional valvular configuration.

In another aspect of the present invention, the second functional valvular configuration is reversibly transformable back to the first pre-implantation configuration.

In a still further aspect of the present invention, the invention is a method comprising acts of: delivering an expandable component distally attached to a distal end of a sheet component to a target area; expanding the expandable component; and positioning the sheet component into the expandable component, such that the positioning induces the sheet component to form a functional valve within the expandable component.

In a still further aspect of the present invention, the act of expanding the expandable component automatically induces the sheet component to position within the expandable component thereby forming a functional valve.

In another aspect of the present invention, the act of positioning the sheet component into the expandable component is manually induced.

In another aspect of the present invention, the method further comprises an act of selectively suturing a proximal end of the sheet.

In another aspect of the present invention, the at least one link is attached to the at least one point of the proximal end of the sheet component by folding, sowing, pinching, suturing, gluing, chemical sealing, mechanically fastening, heat sealing, and any combination thereof.

In another aspect of the present invention, the method further comprises an act of replacing a preexisting natural valve or an artificial valve.

In a still further aspect of the present invention, the invention is a method for manufacturing a valve formed in situ comprising acts of: attaching at least a portion of an expandable component to a distal end of a sheet; fixedly attaching a plurality of portions of a proximal end to itself; and adjoining the distal portion of the sheet component to the distal end of the expandable component.

In another aspect of the present invention, the distal end of the sheet component is adjoined to a distal end of the expandable component by a fiber.

In a still further aspect of the present invention, the invention is an in-situ forming valve, comprising: an expandable component comprising a hollow portion, a distal end, and a proximal end; a plurality of prongs pivotally attached with the distal end of the expandable component; and a sheet component comprising a distal end and a proximal end, the proximal end of the sheet component adjustably attached with the each of the plurality of prongs, the prongs configured to position the proximal end of the sheet component within the hollow portion of the expandable component thereby forming a functional valve in situ.

In a still further aspect of the present invention, the invention is a method for forming a valve in situ comprising acts of: placing a compliant sheet component in contact with a plurality of prongs of an expandable component; using the prongs to pinch the proximal end at the point of contact between each of the prongs and the sheet; expanding the sheet component and expandable component; and inverting the sheet component to form a valve in situ.

In a still further aspect the present invention, the invention is a method for forming a valve in situ comprising acts of: placing a sheet component in contact with a plurality of apexes of an expandable component; fastening the proximal end of the sheet component to itself in at least two locations; expanding the sheet component and expandable component; and turning the sheet component inside out thereby forming a valve in situ.

In another aspect of the present invention, the act of turning the sheet component inside out is automatically triggered by the expansion of the expanding the sheet.

In another aspect of the present invention is an in-situ forming valve, comprising: an expandable component comprising a hollow portion, a distal end, and a proximal end; and a sheet component at least partially attached with the distal end of the expandable component, the sheet component having a first pre-formed configuration and a second functional valvular configuration, the first pre-implantation configuration is configured to transform to the second functional valvular configuration and reversibly transform into the first pre-formed configuration.

BRIEF DESCRIPTION OF THE DRAWINGS

The objects, features and advantages of the present invention will be apparent from the following detailed descriptions of the disclosed aspects of the invention in conjunction with reference to the following drawings, where:

FIG. 2A is a partial side view of a collapsed deployable forming valve system

FIG. 2B is a partial side view of an expanded, formed valve system;

FIG. 8A is an enhanced view of an expanded crown and an unformed sheet;

FIG. 8B is an illustration of one example of an expanded crown and a functional valve; and FIG. 8C is an illustration of an example of an expanded tri-leaflet valve and its annular ring.

Figure 1:
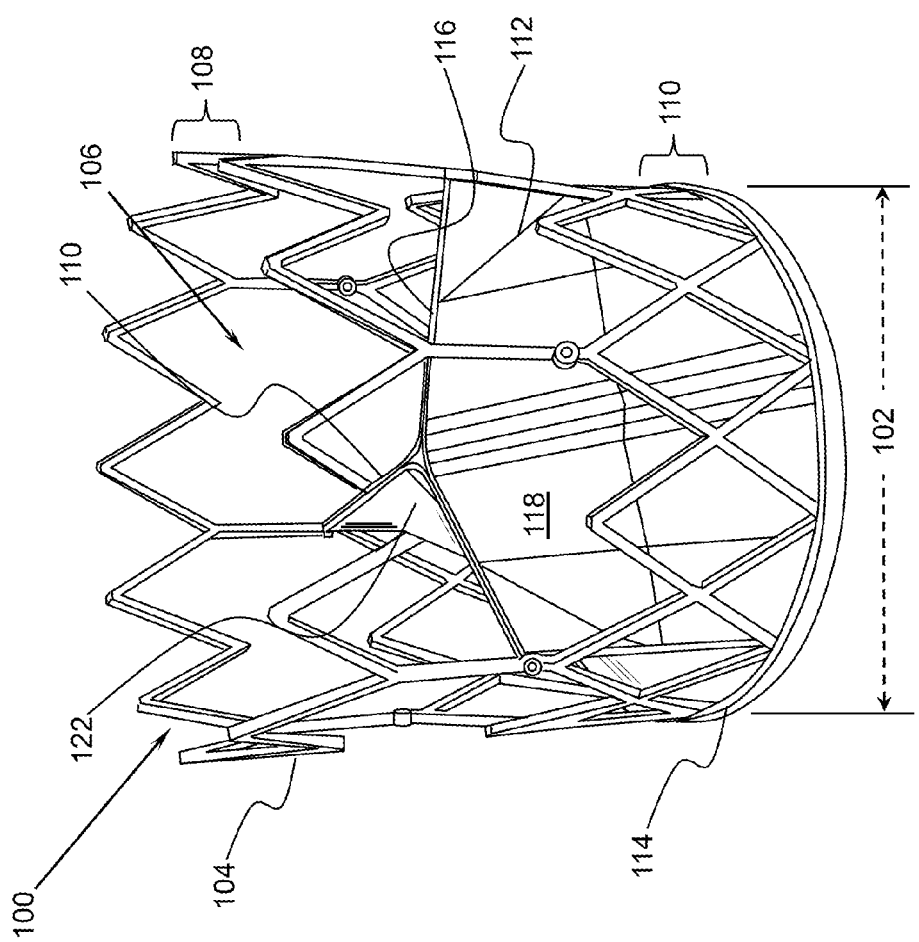
FIG. 1 is a side perspective view of a formed tri-leaflet valve prosthesis.

Appendix A is an additional description of the present invention, entitled, "Deployable forming heart valve system and its percutaneous method of delivery," and Appendix B is a further description of the present invention, entitled, "In-situ formation of a valve by infolding leaflets and its method of delivery."

DETAILED DESCRIPTION

The present invention satisfies the long felt need for a more compact and durable valve which may be formed in situ. The present invention provides a self-deployable valve system, a method of delivery, and a method of manufacturing for the self-deployable valve system. The present invention delivers the necessary components for forming a complete valve system in situ.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Below, an introduction to the present invention is provided to give an understanding of the specific aspects. Then specific embodiments of the present invention are provided.

(1) Introduction

The present invention will now be described more fully hereinafter with reference to the accompanying drawings, in which preferred embodiments of the invention are shown. This invention may be embodied in many different forms and should not be construed as limited to the embodiments set forth herein. Further, the dimensions of layers and other elements shown in the accompanying drawings may be exaggerated to more clearly show the details. The present invention should not be construed as being limited to the dimensional relations shown in the drawings, nor should the individual elements shown in the drawings be construed to be limited to the dimensions shown.

(1.1) In Situ Formed Valve

Referring to FIG. 1, a side perspective view of a second configuration, or expanded state tri-leaflet valve 100 is shown. The valve 100 is a functional, one-way valve which may be fully deployed and assembled in situ. The expandable component 102 of the valve 100 is in a collapsed state as a part of the pre-valve prior to the delivery inside the body. During in situ deployment of the valve 100, the expandable component 102 transforms to an expanded state.

Although shown as a collapsible stent-like frame, the expandable component 102 may take on a variety of forms and may be made from a variety of materials. Non-limiting examples of suitable expandable components 102 include but are not limited to shape-memory materials, stainless steel, polymers, plastic, etc. Further, the expandable component 102 may be made from any number of materials suitable for in vivo and industrial applications. Non-limiting examples of suitable materials include but are not limited to shape memory material, self-expanding Nitinol, or thermal shape memory Nitinol.

The expandable component 102 may also be equipped with at least one bioactive agent. For biologically inspired applications, the expandable component 102 may be equipped with a bioactive agent selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, platelet aggregation inhibitor agents, and antibacterial agents, antiviral agents, antimicrobials, anti-infective agents, and any combination thereof.

The expandable component 102 includes a hollow portion 106, a proximal end 108, and distal end 110. In the case of the assembled, formed valve 100 shown, the distal circumference 114 of the sheet component 112 may extend out from the hollow portion 106 and attached over the distal end 110 of the expandable component 102. Distal circumference 114 overlap of the distal end 110 functionally prevents leakage of fluid such as but not limited to blood along the border of the valve 100. Although the distal end 110 of the expandable component 102 may be a continuous annulus, a continuous shape is not necessary for either deployment or seepage prevention.

The sheet component 112 of the valve 100 is formed into a functional first leaflet 118, second leaflet 110, and third leaflet 122. The first leaflet 118, second leaflet 110, and third leaflet 122 are formed by selectively shaping the proximal circumference 116 at a first shaping point 124, second shaping point 126, and third shaping point 128. In one embodiment, the sheet component 112 may be a single continuous structure. As shown, the proximal circumference 116 is pinched or folded onto itself at the first shaping point 124 and second shaping point 126 to form the first leaflet 118 therebetween. The second leaflet 110 is formed by pinching or folding the proximal circumference 116 at the second shaping point 126 and the third shaping point 128. Similarly, the third leaflet 122 is formed by pinching or folding the proximal circumference 116 at the first shaping point 124 and the third shaping point 128. A shaping point may be temporarily or permanently held in position by either active or passive means. Non-limiting examples of methods by which the shape of the shaping point may be maintained include but are not limited to sutures, bends, fibers, ties, etc.

The sheet component 112 may be made from a variety of materials which may be varied to suit the needs of a particular application. Non-limiting examples of suitable materials include but are not limited to natural membranes, synthetic material, engineered biological tissue, biological valvular leaflet tissue, pericardial tissue, or crosslinked pericardial tissue. In one embodiment, the pericardial tissue may be procured from human, bovine, equine, porcine, ovine, or other animals. In another embodiment, the crosslinked pericardial tissue is crosslinked with a crosslinking agent selected from the group consisting of formaldehyde, glutaraldehyde, dialdehyde starch, antibiotics, glyceraldehydes, cyanamide, diimides, diisocyanates, dimethyl adipimidate, neomycin, carbodiimide, epoxy compound, and any mixture thereof. In an alternative embodiment, the sheet component 112 may be a complex of individual sheets affixed together to form a substantially continuous and leak proof structure. Multiple sheets may be sealed together in a variety of ways. Non-limiting examples of which include but are not limited to glue, epoxy, polymers, latex, etc.

(1.2) Functionality of a Biologically Inspired Prosthetic Valve

The valve 100 may be used in a wide variety of applications. The valve 100 is well suited for a wide variety of industrial applications in which a competent one way valve is needed. The valve 100 is also well suited for biologically inspired valve prosthesis applications. For example, the valve 100 may be used to replace an existing natural valve in the body such as but not limited to heart valves, an existing prosthetic valve, or the valve may be placed in a location where a valve previously did not exist.

When used as a heart valve prosthesis, the valve 100 seamlessly works in place of a natural heart valve. Similar to a natural heart valve, the valve 100 is able to maintain the unidirectional flow of blood from one heart chamber to the next by selectively opening in response to a pressure gradient from one side of the valve to the other.

(1.3) In Situ Formation of a Valve from a Deployable Forming Valve System

Figure 2C:
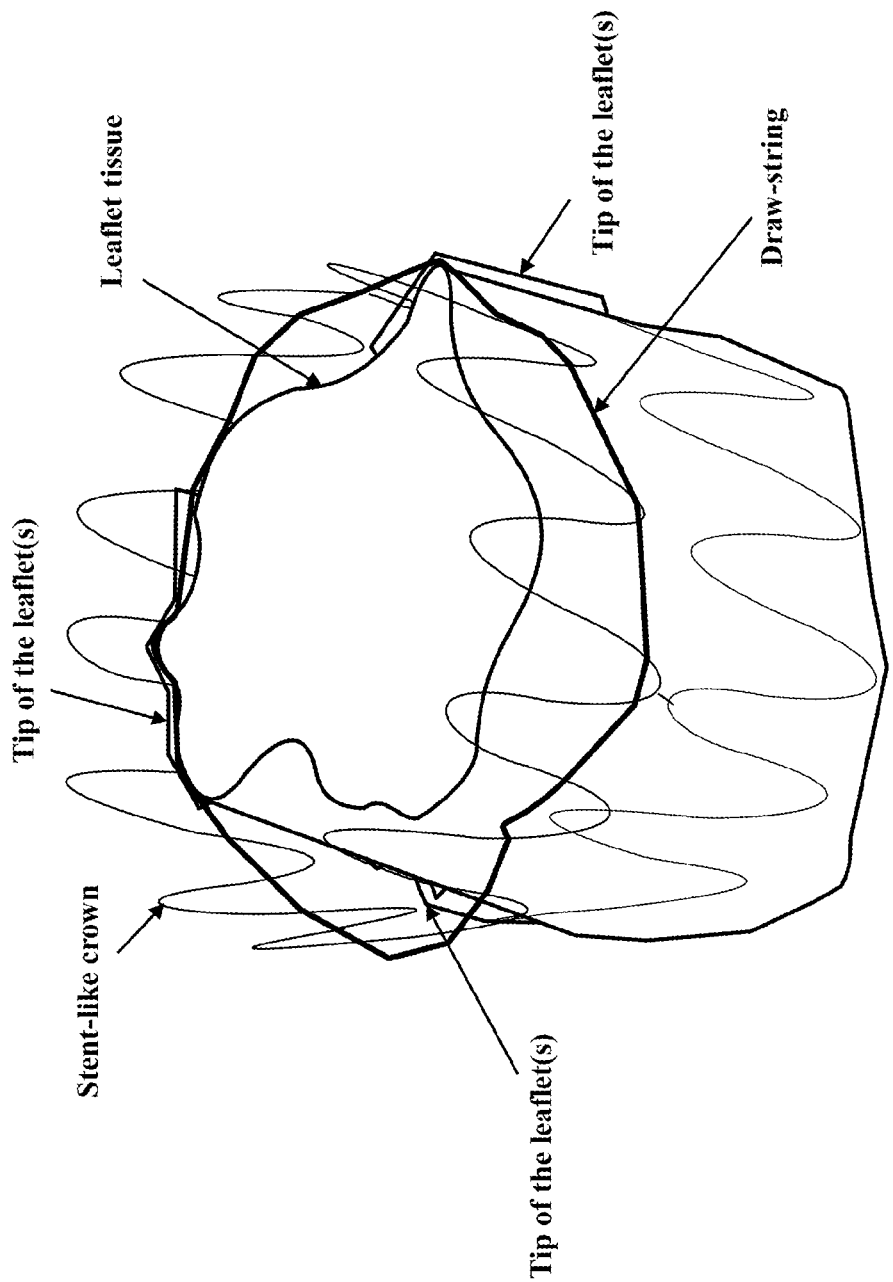
FIG. 2C is the illustration of an example of an expanded component with the leaflet(s)
Figure 2D:
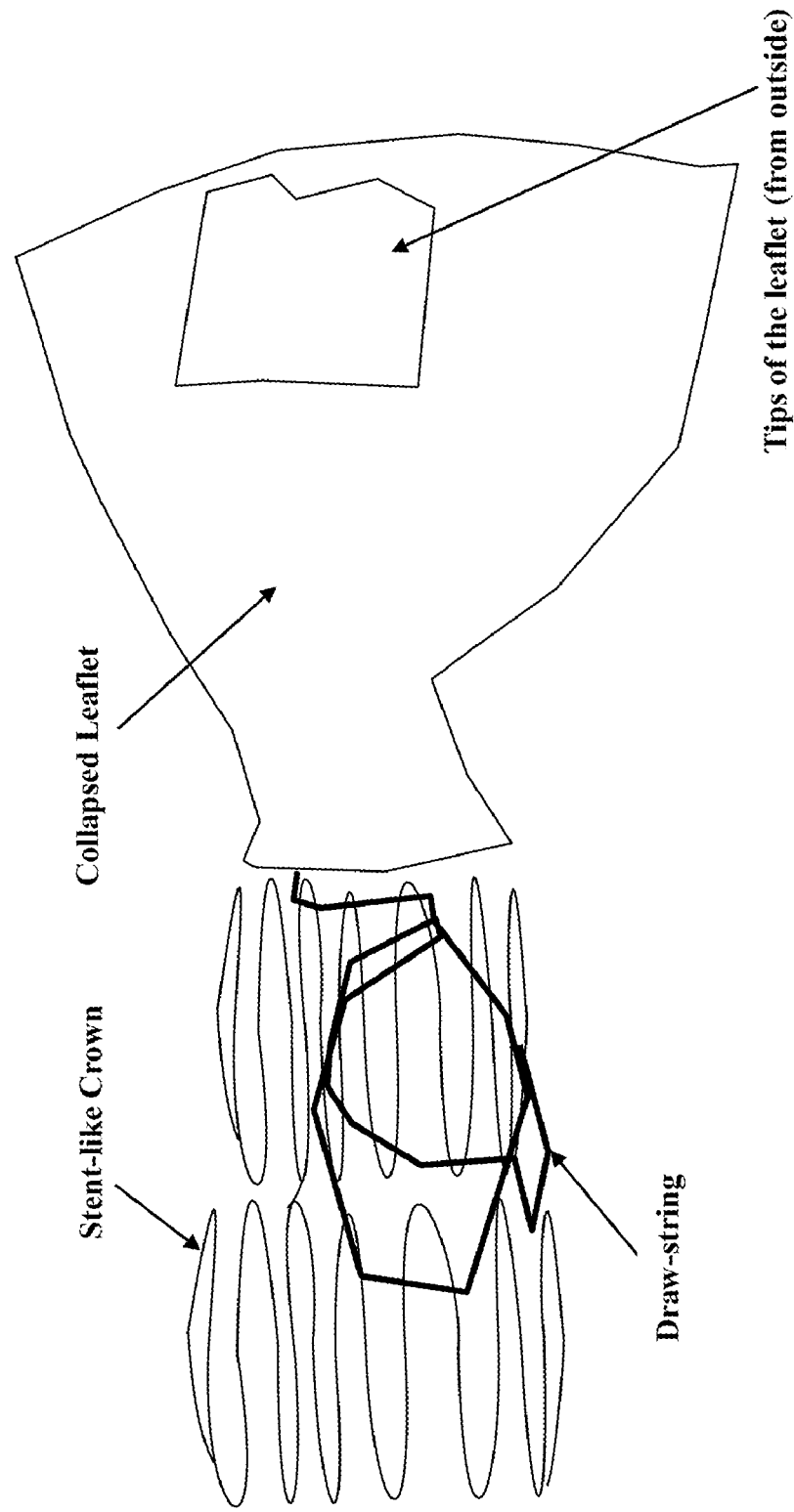
FIG. 2D is the illustration of an example of a collapsed expandable component with the attached compressed leaflet(s)

Referring to FIG. 2A, a collapsed partial side view of a deployable forming valve system 200 is shown. The deployable forming valve system 200 is in a collapsed pre-formed configuration. Importantly, the deployable forming valve system 200 lacks the functionality of a valve while in the pre-formed or radially collapsed state. Further, in the non-functional pre-formed state, the deployable forming valve system lacks the structural characteristics of a valve.

The deployable forming valve system 200 includes an expandable component 210. The expandable component 210 of the deployable forming valve system 200 includes a hollow center or hollow portion 204, a distal end 206, and a proximal end 208. A non-limiting example of a suitable expandable component 210 includes a tube that is shaped into a collapsible/expandable stent-like crown, although in general any piece with suitable attachment points, a hollow center, and the ability to radially expand would be considered a viable alternative. Further, although shown as an elongate and radially collapsed cylinder, the dimensions of the expandable component 210 may be varied to suit a variety of applications.

Attached with and overlapping the bottom circumference, or distal end 206, of the expandable component 210 is the bottom edge or distal end 212 of an unformed leaflet or compliant sheet component 214. The distal end 212 of the compliant sheet component 214 is shown as at least partially overlaping or enveloping the distal end 206 of the expandable component 210.

In the first pre-formed configuration, the proximal end 216 of the compliant sheet component 214 extends downward and beneath the expandable component 210. Although the expandable component 210 and compliant sheet component 214 of the deployable forming valve system 200 are attached, the valve aspect of deployable forming valve system 200 has not been formed and therefore does not function as an operable valve. When the deployable forming valve system 200 is deployed inside the heart, a blood vessel, a lymphatic vessel, or other body channel, the deployable forming valve system 200 is configured to transform to a second functional valvular configuration. Once deployed to the target site and manually or automatically activated, do the pre-valve components of the deployable forming valve system 200 become a fully functional valve. The deployable forming valve system 200 may optionally be removable from the implant site by transforming the device from the second functional valvular configuration back to the first pre-formed configuration of FIG. 2A.

In order to automatically transform the first pre-formed configuration to a second functional valvular configuration, a variety of mechanisms may be used. A non-limiting example of a suitable mechanism includes using a link 218. The link 218 may accomplish this task with a minimal number of attachment points. Non-limiting examples of suitable link 218 materials include but are not limited to natural or synthesized fiber, metal, or plastic, and elastic/non-elastic fibers such as but not limited to silk, Nitinol, and polymeric materials. When using a link 218, the proximal end 208 of the expandable component 210 is attached to one end of a link 218, such as a string, while the other end of the link 218 is attached to the proximal end 216 of the compliant sheet component 214. By radially expanding the diameter 202 of the expandable component 210, the link 218, attached with the proximal end 216 of the compliant sheet component 214, positions or draws the compliant sheet component 214 into the hollow portion 204 of the expandable component 210. As the proximal end 216 of the compliant sheet component 214 is drawn or positioned into the hollow portion 204 proximally, the compliant sheet component 214 is pulled inside-out.

The collapsed state of the deployable forming valve system 200 is suitable for delivery to a desired target area. While in the first pre-formed configuration, the diameter 202 of the deployable forming valve system 200 is compressed to the lower limit of the deployable forming valve system 200. Although the deployable forming valve system 200 is non functional, the compressed diameter 202 facilitates the difficult task of traveling along narrow tubular, channels, veins, or arteries as the valve prosthesis is moved towards the target area.

Further information regarding a deployable forming heart valve system and its percutaneous method of delivery can be found in Appendix A, which is incorporated by reference as though fully set forth herein. Appendix A is the content of a provisional application to which this application claims priority.

Referring to FIG. 2B, a partial side view of an expanded valve prosthesis 220 is shown. While the expandable component 222 is expanding, the diameter 224 increases, turning the compliant sheet component 226 inside out and into the hollow portion 228 of the expandable component 222. By synchronizing the expansion of the expandable crown with the positioning of the compliant sheet component 226 via a contraction system such as a link 220, the formation of the second functional valvular configuration may be completely automated. While the expandable component 222 is expanded at the designated position, the draw-string at the proximal section of the crown pulls the compliant sheet component 226 inside out through the expandable component 222. Examples of a suitable expansion mechanism include but are not limited to an expandable component 222 made from shape memory material or an inflatable balloon.

The automated or programmed formation of the functional valvular configuration from primary pre-valve configuration may be enhanced by an expandable component 222 which is forcibly compressed while in transit to the target deployment site. Once at the target site, the expandable component 222 is allowed to return to its natural expanded state, for example the formed, functional valvular configuration of FIG. 2B. Such activation transform may be accomplished by removing a physical restraint securing the first pre-implantation configuration 200. Automatic activation of the expandable component may be accomplished by modifying the characteristics of the materials used in the expandable component 222. Non-limiting examples of suitable expandable component 222 materials include but are not limited to stainless steel, shape-memory materials, superelastic materials and magnetic-shape-memory materials.

Figure 3B:
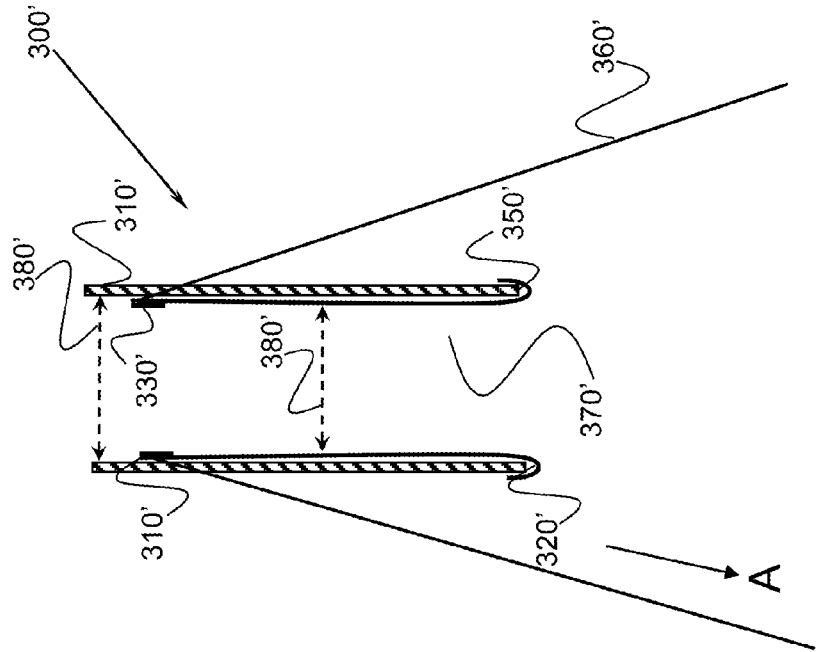
FIG. 3B is the partial side-view diagram of one example of an expanded, formed valve.
Figure 3A:
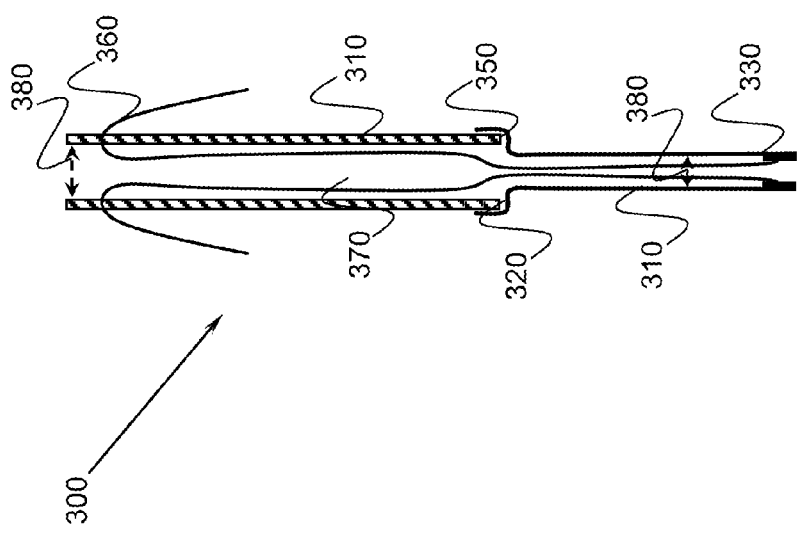
FIG. 3A is the partial side-view diagram of one example of a collapsed valve.

Referring to FIG. 3A, a partial side view of a collapsed manually deployable valve 300 is shown. The manually deployable valve 300 consists of two major components: a superior stent-like crown 310, and an inferior leaflet membrane 320. In the collapsed state, the crown 310 is constricted over a delivery catheter/guide-wire while the leaflet membrane 320 is wrinkled at the distal end 330 and proximal end 330. The manually deployable valve 300 is deliverable to its designated position transapically or via major vessels such as but not limited to femoral artery, carotid artery, and jugular vein.

The distal end 350 of the stent-like crown or expandable component 310 is connected to the distal end 330 of the leaflet membrane 320. The proximal end 330 of the unformed leaflet membrane 320 is proximally anchored to a contraction system such as a link 360 in the form of a draw-string or combination of pulling strings. Further, the link 360 may be a singular link 360 detachably attached to at least one point of contact along the proximal end 330 of the unformed leaflet membrane 320. Ultimately the formation of the leaflets, such as those shown in FIG. 1, may be manually performed or triggered independent of the expansion of the stent-like crown 310. For example, as the diameter 380 of the stent-like crown 310 is increasing, the diameter 390 of the leaflet membrane 320 also increases. Unlike the automatic formation of the second functional valvular configuration depicted in FIG. 3B, the proximal end 330 of the leaflet membrane 320 is manually positioned into the hollow portion 370 of the stent-like crown 310 by pulling the link 360. The link 360 is configured to position the proximal end 330 of the leaflet membrane 320 into the hollow portion 370 of the stent-like crown 310 thereby forming a tri-leaflet valve in situ.

Referring to FIG. 3B, a partial side view of the expanded, manually deployable valve 300' is shown. The stent-like crown 310' of the valve 300' may be expanded by any number of methods including but not limited to balloon catheters and other suitable expansion instruments. The stent-like crown 310' may also be made of a shape memory material or elastic material. Once the collapsed stent-like crown 300' has been delivered to the target site, the collapsed stent-like crown 300' is transformed to its expanded configuration 310. Attached to the distal end 350' of the stent like crown 310' is a portion of the leaflet membrane 320'. As the diameter 380' of the stent-like crown 310' increases, the diameter 390' of the leaflet membrane 320' also increases until the distal end 330' and proximal end 330' are fully opened (not shown in the picture). Once fully deployed, a contraction system, such as a link 360', is pulled downward in the direction of A. By pulling the link 360' in the direction of A, the open leaflet membrane 320' is positioned into the hollow portion 370', thereby forming a fully functional valve 300'.

Figure 4:
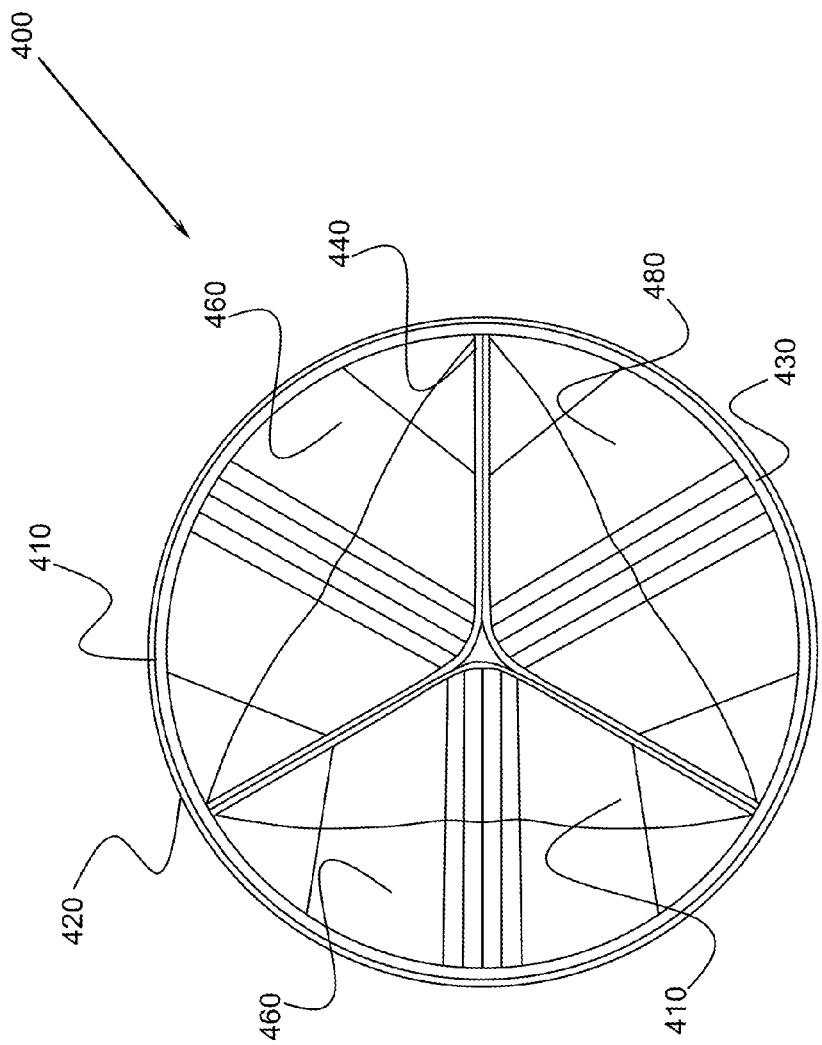
FIG. 4 is a top perspective view of an expanded tri-leaflet valve prosthesis.

A top perspective view of a tri-leaflet valve 400 is shown in FIG. 4. As shown, both the crown 410 and membrane(s) 420 have been expanded and formed into a fully functional tri-leaflet valve prosthesis 400. The distal end 430 of the membrane 420 is shown overlapping the distal end and side walls of the crown 410. The proximal end 440 of the crown 410 and the proximal end 440 of the membrane 420 are also clearly visible. The proximal end 440 of the membrane 420 defines the first leaflet 460, the second leaflet 470, and the third leaflet 480. The distal end 430 of the membrane 420 may be attached to the distal end of the crown 410 by mechanisms including, but not limited to, sewing, sutures or stitches, adhesives, or frictional fit depending on the particular application.

(1.4) Delivery of an In Situ Formed Valve Prosthesis

Figure 5:
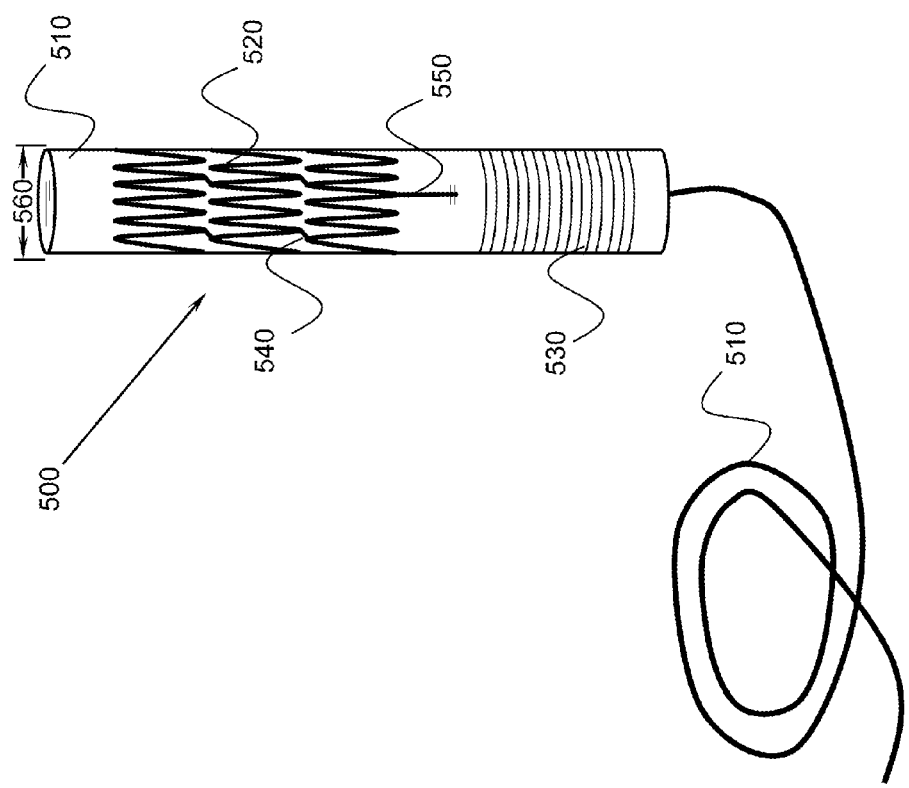
FIG. 5 is a side-view of a collapsed a pre-formed valve prosthesis.

FIG. 5 demonstrates another embodiment of the present invention referred to as the pre-formed valve system 500, deliverable and consequently deployable inside the target site within a body chamber, vessel, etc. Referring to FIG. 5, the subcomponents of a pre-valve system 500 over a partial segment of a delivery catheter are shown. The pre-valve system 500 is deliverable into a chamber in a collapsed state and transforms into a second functional valvular configuration. Although shown as a catheter 510 and guide-wire 520 assembly, a variety of instruments may be used to deliver and deploy the collapsed configuration of the valve inside the target site.

The pre-valve system 500 includes an expandable component, shown as a compressed crown 530, and a sheet component in the form of a compressed and compliant membrane 540. The compliant membrane 540 may be made of thin sheet component which is appended over the catheter 510. The compressed crown 530 is comprised of multiple segments held together with joints 550. A contraction system, such as a plurality of prongs 550 may be attached at the proximal end of the compressed crown 530. The prongs 550 act as a link which may be attached to at least one point of the proximal end of the compliant membrane 540. The prongs 550 may be attached to at least one point of the compliant membrane 540 by folding, sowing, pinching, suturing, gluing, chemical sealing, mechanically fastening, heat sealing, or any combination thereof.

The compliant membrane 540 may be made from compliant tissue membranes, which can be a single sheet component or a compound manifold. The compliant membrane 540 may also be made from a variety of materials such as but not limited to polymeric materials or obtained from bovine, porcine or equine pericardial tissue, depending on the type of usage.

In a first step the subcomponents of the unassembled pre-valve system 500 are placed on the catheter 510 or a reasonable assembly or delivery system alternative. The compressed crown 530 and compliant membrane 540 are placed unassembled on the catheter 510. The diameter 570 of the unassembled pre-valve system 500 is sufficiently small to suite a wide variety of applications. Further the relatively small diameter 570 of the unassembled pre-valve system 500 eases the task of traversing great distances in confined channels while the unassembled pre-valve system 500 is delivered towards the target site.

Figure 6:
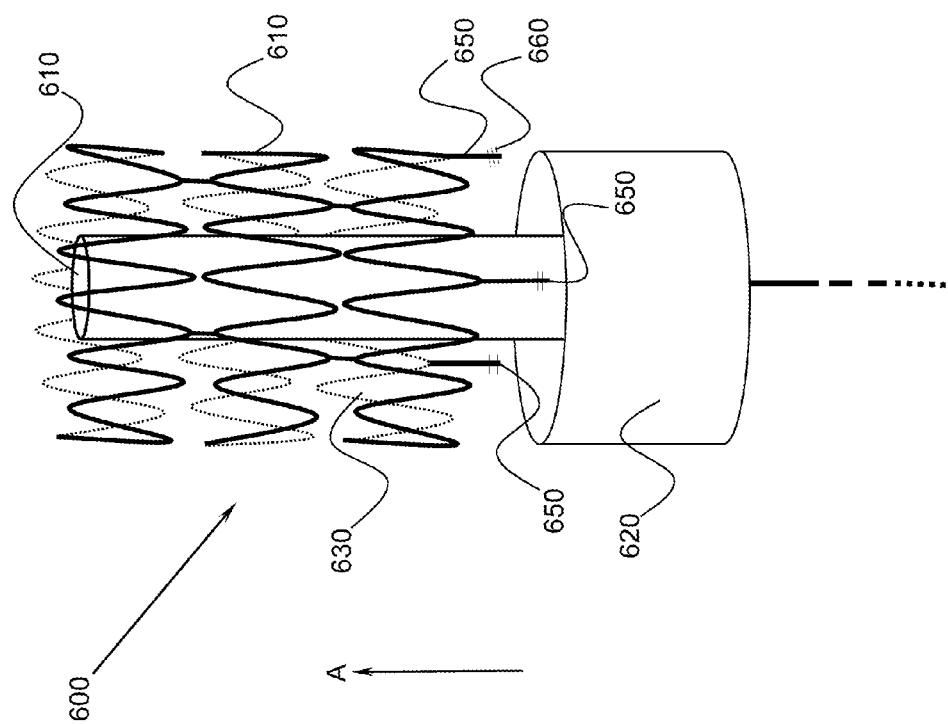
FIG. 6 is a side view of a stage of an expanding forming valve prosthesis.

FIG. 6 is a transitional time-point during the transformation process of the pre-valve configuration to expanded valve configuration. Once at the target site, the subcomponents of the pre-valve configuration 600 are expanding from the catheter 610 as shown in FIG. 6. The fenestrated shape of the crown 620 provides an adequate attachment surface for deployment in soft substrates such as but not limited to calcified tissue, normal, tissue, etc. Although a fenestrated crown 620 is shown, a variety of mechanisms may be used in addition to or in place of a fenestrated crown 620. Non-limiting examples of which include, but are not limited to a monolithic stent-like component, a structure mainly made of multitude of woven wires, etc. Once the fenestrated component 620 is secured to the target site, the sheet component or unformed leaflets 630 are moved in the direction of A over the circumference of the crown 620 and over the prongs 650. The unformed leaflets 630 are comprised of a skirt, a role or a tubular sheet component of compliant membrane folded over the catheter 610 beside or adjacent the fenestrated crown 620. The prongs 650 along the fenestrated crown 620 will act as the support for valve's leaflets 630.

Each of the three prongs 650 is adapted with a series of grips 660 adapted to secure at least a portion of the sheet component or unformed leaflets 630 within their grasp. The grips 660 are configured to secure and fasten the shaping points along the perimeter of the unformed leaflets 630. The shaping points are folded onto themselves, such that when the prongs 650 are activated, the shaping points induce the unformed leaflets 630 to form a functional valve.

Figure 7:
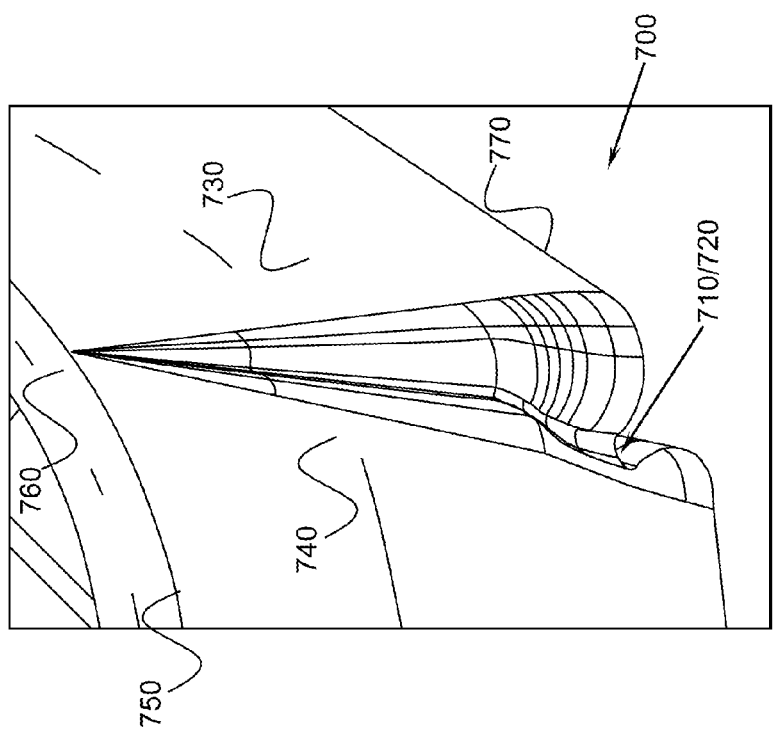
FIG. 7 is a zoomed in view of a valve leaflet(s)' membrane.

An enhanced view of a sheet component 700 with a fold 710 is shown in FIG. 7. The fold 710 of the sheet component 700 is formed at the forming point 720. The fold 710 at the forming point 720 may be induced by a link 260 (See FIG. 2B) or a prong 550 (See FIG. 5) in contact with the sheet component 700. As the sheet component 700 is positioned within an expandable component or ring (not shown), the sheet component 700 to the left and right of the fold 710 become a first leaflet 730 and second leaflet 740 respectively. In order to form the first leaflet (or a segment of a single piece leaflet) 730 and second leaflet (or another segment of the same single piece leaflet) 740, the distal end 750 is brought into contact with the expandable component 760 thereby securing the distal end 750 of the sheet component 700 in place. Once the distal end 750 of the sheet component 700 is secured in place, a link or prong pulls or positions the proximal end 770 of the sheet component 700 into the expandable component 760 thereby forming a bicuspid valve within the hollow part of the expandable component 860 (or crown) at the target site.

The expanding non-functional configuration is sequentially transitioned towards a second functional valvular configuration. The transition begins with the expansion of the crown 620 and sheet component 730 (See FIG. 7), the prongs 650 are used to create a fold, such as the fold 710 depicted in FIG. 7 and to secure the leaflets preventing valve prolapse. An enhanced view of an expanded crown 800 and unformed sheet component 810 in contact with the prongs 820 is depicted in FIG. 8A. Each of the three prongs 820 attached to the unformed sheet component 810 creates a fold 830 in the material. The prongs 920 may be used to carry and deliver permanent sutures or fasteners to hold or grip the fold 830 of the sheet component 810. The prongs 820 may either be removably or permanently affixed to the sheet component 810 at the fold 830 by shape memory and/or regular sutures. Once the folds 830 have been secured, the prongs 820 push or position the sheet component 810 into the expanded crown 800 in the direction of A, ultimately forming the valve 840 depicted in FIG. 8B.

Referring to FIG. 8B, the expanded crown 800' and fully functional valve 840 are shown. The functional valve 840 is shown with three leaflets (or a tubular leaflet with three pinches) 850. The expanded crown 800' fits within the channel of the target area, while fluids are selectively allowed to pass through the valve 840. The expanded crown 800' resists the recoil force preventing wall collapse, secures the position of the valve 840 placement, and may prevent or minimize the process of tissue overgrowth and its impact on the functionality of the implanted valve 840 through drug and/or gene coating. The distal end overlap 860 of the valve 840 extends over the expanded crown 800' and functions akin to an O-ring to prevent seepage along the wall of the expanded crown 800'. For example, when used to replace an existing heart valve in body, the distal end overlap 860 of the valve 840 prevents paravalvular leakage and regurgitation. In one embodiment, a hollow annulus or support structure 870 may be placed inside the expanded crown 800' and over the valve 840. For applications in which the expanded crown 800' are not needed, the support structure 870 may be placed over the valve 840 and secured within the distal end overlap 860.

FIG. 8C is an illustration of an expanded tri-leaflet valve 840' having three leaflets or a single tubular leaflet with 3 pinches 850' supported by an annular ring 870' enveloped by a distal end overlap 860'. An annular ring 870' may be secured to at least one location to the distal end overlap 860'. The annular ring 870' would aide the valve 840' in resisting recoil and provides a structure by which the valve 840' could be secured to the target position.

Further description of the in situ formation of a valve and its method of delivery can be found in Appendix B, which is incorporated by reference as though fully set forth herein. Appendix B is also the content of a provisional application to which this application claims priority.

What is claimed is:

1. An in-situ forming valve, comprising:
   an expandable component comprising a hollow portion, a distal end, and a proximal end;
   a sheet component comprising a distal circumference and a proximal end, the distal circumference held in at least partial contact with the distal end of the expandable component, the proximal end of the sheet component further comprising at least two pinched regions; and
   an at least one link attached to at least one point of the proximal end of the sheet, the link attached with the expandable component, the expandable component and link adapted to draw the proximal end of the sheet component into the hollow portion of the expandable component upon expansion of the expandable component, thereby forming a functional valve in situ.

2. The apparatus of claim 1, wherein the sheet component comprises a single tubular sheet.

3. The apparatus of claim 1, wherein the skeet component is a multitude of sheet components seated together.

4. The apparatus of claim 1, wherein the expandable component is at least partially comprised of a shape memory material.

5. The apparatus of claim 1, wherein the expandable component is at least partially comprised of an elastic material.

6. The apparatus of claim 1, wherein the expandable component is equipped with at least one bioactive agent selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, platelet aggregation inhibitor agents, antibacterial agents, antiviral agents, antimicrobials, and anti-infectives.

7. The apparatus of claim 1, wherein the sheet component is made from a material selected from a group consisting of natural membranes, synthetic material, engineered biological tissue, biological valvular leaflet tissue, pericardial tissue, and cross-linked pericardial tissue.

8. The apparatus of claim 1, further comprising an elongate delivery apparatus, wherein the in-situ formed valve is collapsibly mounted onto the elongate delivery apparatus.

9. The apparatus of claim 1, wherein the distal end of the at least one hollow sheet component at least partially extends out from the hollow portion and over the distal end of the expandable component.

10. The apparatus of claim 1, wherein the at least one link is detachably attached to at least three points of contact along the proximal end of the sheet, the link configured to position the proximal end of the sheet component into the hollow portion of the expandable component, thereby forming a three flap valve in situ.

11. The apparatus of claim 1, wherein the at least one link is made of a dissolvable material.

12. An in-situ forming valve, comprising:
- an expandable component comprising a hollow portion, a distal end, and a proximal end; and
- a sheet component at least partially enveloping the distal end of the expandable component, the sheet component having a first pre-implantation configuration and a second functional valvular configuration, the first pre-implantation configuration is configured to transform to the second functional valvular configuration; and
- wherein the expandable component and sheet component are adapted to draw the sheet component into the hollow portion of the expandable component upon expansion of the expandable component and thereby transform the sheet component into the second functional valvular configuration.

13. The apparatus of claim 12, wherein the second functional valvular configuration is reversibly transformable back to the first pre-implantation.

14. An in-situ forming valve, comprising:
- an expandable component comprising a hollow portion, a distal end, and a proximal end;
- a plurality of prongs pivotally attached with the distal end of the expandable component; and
- a sheet component comprising a distal end and a proximal end, the proximal end of the sheet component adjustably attached with the each of the plurality of prongs, the prongs adapted to position the proximal end of the sheet component within the hollow portion of the expandable component upon expansion of the expandable component to form a functional valve in situ.

15. An in-situ forming valve, comprising:
- an expandable component comprising a hollow portion, a distal end, and a proximal end; and
- a sheet component at least partially attached with the distal end of the expandable component, the sheet component having a first pre-formed configuration and a second functional valvular configuration, the first pre-implantation configuration is configured to transform to the second functional valvular configuration and reversibly transform into the first pre-formed configuration; and
- wherein the expandable component and sheet component are adapted to draw the sheet component into the hollow portion of the expandable component upon expansion of the expandable component and thereby transform the sheet component into the second functional valvular configuration.

* * * * *